United States Patent [19]

Kuberasampath et al.

[11] Patent Number: 6,077,823

[45] Date of Patent: *Jun. 20, 2000

[54] METHOD FOR REDUCING TISSUE DAMAGE ASSOCIATED WITH ISCHEMIA-REPERFUSION OR HYPOXIA INJURY

[75] Inventors: Thangavel Kuberasampath, Medway, Mass.; Roy H. L. Pang, Etna, N.H.; Hermann Oppermann, Medway, Mass.; David C. Rueger, Hopkinton, Mass.; Charles M. Cohen, Medway, Mass.; John E. Smart, Weston, Mass.

[73] Assignee: Creative BioMolecules, Inc., Boston, Mass.

[ * ] Notice: This patent is subject to a terminal disclaimer.

[21] Appl. No.: 08/445,467

[22] Filed: May 22, 1995

Related U.S. Application Data

[63] Continuation of application No. 08/165,511, Dec. 9, 1993, abandoned, which is a continuation of application No. 07/938,336, Aug. 28, 1992, abandoned, which is a continuation-in-part of application No. 07/753,059, Aug. 30, 1991, abandoned, and application No. 07/752,764, Aug. 30, 1991, abandoned, which is a continuation-in-part of application No. 07/667,274, Aug. 30, 1991, abandoned.

[51] Int. Cl.[7] .......................... A61K 38/17; A61K 38/18

[52] U.S. Cl. .................................. 514/12; 514/2; 514/8

[58] Field of Search .................. 514/2, 8, 12; 435/69.4, 435/172.3; 530/399

[56] References Cited

U.S. PATENT DOCUMENTS

| | | | |
|---|---|---|---|
| 4,806,523 | 2/1989 | Bentz et al. ............................... | 514/2 |
| 4,877,864 | 10/1989 | Wang et al. ............................... | 514/12 |
| 4,968,590 | 11/1990 | Kuberasampath et al. ............. | 530/326 |
| 4,971,952 | 11/1990 | Bentz et al. ............................... | 514/12 |
| 4,975,526 | 12/1990 | Kuberasampath et al. ............. | 530/350 |
| 5,002,965 | 3/1991 | Ramwell et al. ....................... | 424/423 |
| 5,011,691 | 4/1991 | Oppermann et al. ................... | 424/423 |
| 5,013,649 | 5/1991 | Wang et al. ............................ | 435/69.1 |
| 5,091,513 | 2/1992 | Huston et al. ........................... | 424/423 |
| 5,106,626 | 4/1992 | Parsons et al. ......................... | 424/423 |
| 5,108,753 | 4/1992 | Kuberasampath ...................... | 424/422 |
| 5,118,791 | 6/1992 | Burnier et al. .......................... | 530/326 |
| 5,135,915 | 8/1992 | Czarniecki et al. .................... | 514/21 |
| 5,141,905 | 8/1992 | Rosen et al. ........................... | 435/69.1 |
| 5,202,311 | 4/1993 | Folkman et al. ......................... | 514/12 |
| 5,221,734 | 6/1993 | Burk et al. ............................. | 530/399 |
| 5,972,884 | 10/1999 | Cohen et al. ............................ | 512/12 |

FOREIGN PATENT DOCUMENTS

| | | |
|---|---|---|
| 0148155 | 1/1985 | European Pat. Off. . |
| 0 269 408 | 6/1988 | European Pat. Off. . |
| 0416578 | 9/1990 | European Pat. Off. . |
| WO94/01106 | 3/1984 | WIPO . |
| 88/00205 | 1/1988 | WIPO . |
| 89/09787 | 10/1989 | WIPO . |
| 89/09788 | 10/1989 | WIPO . |
| 89/10409 | 11/1989 | WIPO . |
| 90/00900 | 2/1990 | WIPO . |
| 90/03733 | 4/1990 | WIPO . |
| 91/05802 | 5/1991 | WIPO . |
| 92/07073 | 4/1992 | WIPO . |
| 92/15323 | 9/1992 | WIPO . |

OTHER PUBLICATIONS

Behringer et al., *Nature,* 345:167–170 (1990).
Cate et al., *Cell,* 45:685–698 (1986).
Celeste et al., *PNAS,* 87:9843–9847 (1990).
Green et al., *Nature,* 347:391–394 (1990).
Kuberasampath et al., *J. Biol. Chem.,* 265:13198–13205 (1990).
Lee, *Molecular Endocrinology,* 90:1034–1040 (1990).
Lee, *PNAS,* 88: 4250–4254 (1991).
Lyons et al., *PNAS,* 86:4554–4558 (1989).
Lyons et al., *Genes & Development,* 3:1657–1668 (1989).
Mason et al., *Nature,* 318:659–663 (1985).
Mason et al., *Mol. Endocrinology,* 3:1352–1358 (1989).
Miller et al., *Cancer Research,* 42:2589–3594 (1987).
Ozkaynak et al., *Embo J.,* 9:2085–2093 (1990).
Ozkaynak et al., *Biochem. Biophys. Res. Comm.,* 179:116–123 (1991).
Padgett et al., *Nature,* 325:81–34 (1987).
Panganiban et al., *Mol. and Cell. Biol.,* 10:2669–2677 (1990).
Sampath et al., *PNAS,* 80:6591–6595 (1983).
Schbert et al., *Nature,* 344:868–870 (1990).
Smith et al., *Nature,* 345:729–731 (1990).
Sokol et al., *Science,* 249:561–563 (1990).
Wang et al., *PNAS,* 87:2220–2224 (1990).
Wang et al., *PNAS,* 85:9484–9488 (1988).
Weeks, *Cell,* 51:861–867 (1987).
Wharton et al., *PNAS,* 88:9214–9218 (1991).
Wozney et al., *Science,* 242:1528–1534 (1988).
Yannas, *Angew. Chem. Int. Ed. Engl.,* 29:20–35 (1990).
Lefer et al., *Science,* vol. 249, No. 4964, pp. 61–64, Jul. 6, 1990.
Kuruvilla et al., *Proc. Natl. Acad. Sci. USA,* vol. 88, No. 7, pp. 2918–2921, Apr. 1991.
Wozney et al. (1990), "Growth Factors Influencing Bone Development," 13 *J. Cell Sci. Suppl.* 149–156.
Celeste et al. (1990), "Identification of Transforming Growth Factor β Family Members Present in Bone–Inductive Protein Purified From Bovine Bone," 87 *PNAS* 9843–9847.
Takuwa et al. (1991), "Bone Morphogenetic Protein–2 Stimulates Alkaline Phosphatase Activity and Collagen Synthesis in Cultured Osteoblastic Cells, MC3T3–E1," 174 *Biochem. Biophys. Res. Comm.* 1:96–101.

(List continued on next page.)

*Primary Examiner*—Elizabeth C. Kemmerer
*Attorney, Agent, or Firm*—Ivor R. Elrifi; Michel Morency; Mintz, Levin, Cohn, Ferris, Glovsky and Popeo, P.C.

[57] ABSTRACT

The present invention is directed to methods and compositions for alleviating tissue destructive effects associated with the inflammatory response to tissue injury in a mammal. The methods and compositions include administering a therapeutically effective concentration of a morphogen or morphogen-stimulating agent sufficient to alleviate immune cell-mediated tissue destruction.

12 Claims, 6 Drawing Sheets

OTHER PUBLICATIONS

Yamaguchi et al. (1991), "Recombinant Human Bone Morphogenetic Protein–2 Stimulates Osteoblastic Maturation and Inhibits Myogenic Differentiation In Vitro," 113 *J. Cell Biol.* 3:681–687.

D'Allesandro et al. (1991), Abstract Q–105 *J. Cell. Biochem.*

Israel et al. (1991), Abstract Q–111 *J. Cell. Biochem.*

Thies et al. (1992), "Recombinant Human Bone Morphogenetic Protein–2 Induces Osteoblastic Differentiation in W–20–17 Stromal Cells," 130 *Endocrinology* 3:1318–1324.

Wozney et al. (1992), "The Bone Morphogenetic Protein Family and Osteogenesis," 32 *Mol. Reprod. Dev.* 2:160–167.

Rogers et al. (1992), "Bone Morphogenetic Proteins–2 and –4 are Involved In The Retinoic Acid–Induced Differentiation of Embryonal Carcinoma Cells," 3 *Mol. Biol. Cell* 2:189–196.

Wozney et al, ; Celeste et al.; Rosen et al. (1992), Abstracts 76(WO26), 100(W502) and 103(W513) *J. Cell Biochem, Suppl.* 16 Part F.

Israel et al. (1992), "Expression and Characterization of Bone Morphogenetic Protein–2 in Chinese Hamster Ovary Cells," 7 *Growth Factors* 139–150.

Padgett et al. (1993), "Human BMP Sequences Can Confer Normal Dorsal–Ventral Patterning in the Drosophila Embryo," 90 *PNAS* 2905–2909.

Wozney et al. (1988), "Novel Regulators of Bone Formation: Molecular Clones and Activities," 242 *Science* 1528–1534.

Wang et al. (1988), "Purification and Characterization of Other Distinct Bone–Inducing Factors,";0 85 *PNAS* 9484–9488.

Rosen et al. (1989), "Purification and Molecular Cloning of a Novel Group of BMPS and Localization of BMP MRNA In Developing Bone," 20 *Connect. Tissue Res.* 1–4:313–319.

Wozney et al. (1990), "Bone Morphogenic Proteins," 1 *Prog. In Growth Factor Res.* 267–280.

Wang et al. (1990), "Recombinant Human Bone Morphogenetic Protein Induces Bone Formation," 87 *PNAS* 2220–2224.

Rosen et al.; Celeste et al. (1990), 2 Abstracts *J. Cell Biochem, Suppl.* 14 Part E, 004:33; 54:105.

Katagiri et al. (1990), "The Non–Osteogenic Mouse Pluripotent Cell Line, C3H10T1/2 is Induced to Differentiate Into Osteoblastic Cells by Recombinant Human Bone Morphogenetic Protein–2," 172 *Biochem. Biophys. Res.* 1:295–299.

Hammond et al. Can J. Physiol. Pharmacol. 63:173–187, 1985.

Bowie et al. Science 247:1306–1310, 1990.

Sampath et al. (1983), "Homology of Bone–Inductive Proteins From Human, Monkey, Bovine, and Rat Extracellular Matrix," 80 *Proc. Nat'l. Acad. Sci. USA* 6591–6595.

Bentz et al. (1987), "Cartilage Induction and Differentiation: The Role of Bone Derived Cartilage Inducing Factor (CIF–A)," *Dev. & Diseases of Cartil. & Bone Matrix* 137–147.

Ruscetti et al. (1991), "Transforming Growth Factor–$\beta$ And The Immune System," 3 *Prog. Growth Factor Res.* 159–175.

Sporn et al. (1992), "Transforming Growth Factor–$\beta$: Recent Progress and New Challenges," 119 *J. Cell Biol.* 1017–1021.

Gross et al. (1993), "Transforming Growth Factor–$\beta$1 Reduces Infarct Size After Experimental Cerebral Ischemia in a Rabbit Model," 24 *Stroke* 558–562.

Reddi et al. (1993), "Initiation and Promotion of Bone Differentiation by Bone Morphogenetic Proteins," 8 *J. Bone Min. Res.* 2:S499–S502.

Sampath et al. (1994), "Structure, Function, and Orthopedic Applications of Osteogenic Protein–1 (OP–1)," *Complications in Orthop.* 101–107.

Deininger et al. (1995), "Detection of Two Transforming Growth Factor–$\beta$–Related Morphogens, Bone Morphogenetic Proteins –4 and –5, in RNA of Multiple Sclerosis and Creutzfeldt–Jakob Disease Lesions," 90 *Acta Neuropathol.* 76–79.

Schluesener et al. (1995), "Immunolocalization of BMP–6, a Novel TGF–$\beta$–Related Cytokine, in Normal and Atherosclerotic Smooth Muscle Cells," 113 *Atherosclerosis* 153–156.

Schluesener et al. (1995), "Immunolocalization of vgr (BMP–6, DVR–6), a TGF–$\beta$–Related Cytokine, to Schwann Cells of the Rat Peripheral Nervous System: Expression Patterns Are Not Modulated by Autoimmune Disease," 13 *GLIA* 75–78.

Noda et al. Endocrinology 124:2991–2994, 1989.

Joyce et al. Annals of the New York Academy of Sciences 593:107–123, 1990.

Beck et al. J. Bone Min. Res. 6: 1257–1265, 1991.

Puolakkainen et al. J. Surg. Res. 58:321–329, 1995.

Gennaro (1990) Remington's Pharmaceutical Sciences (Mack Pubs., N.Y.).

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ1
            /note= "WHEREIN EACH XAA INDEPENDENTLY INDICATES
            ONE OF THE 20 NATURALLY-OCCURING L-ISOMER, A-AMINO
            ACIDS, OR A DERIVATIVE THEREOF."

(xi) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Cys Xaa Xaa Xaa Cys Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Cys Cys Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Cys Xaa Cys
                 85                  90                  95

Xaa
```

(2) INFORMATION FOR SEQ ID NO:2:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ2
            /note= "WHEREIN EACH XAA INDEPENDENTLY INDICATES
            ONE OF THE 20 NATURALLY OCCURING L-ISOMER A-AMINO
            ACIDS, OR A DERIVATIVE THEREOF."

(xi) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa Xaa
 1               5                  10                  15
Xaa Xaa Xaa Xaa Xaa Xaa Xaa Xaa Cys Xaa Xaa Xaa Cys Xaa Xaa Xaa
             20                  25                  30
Xaa Xaa Xaa Cys Xaa Xaa Xaa Xaa Xaa Xaa Xaa Xaa Xaa Xaa Xaa Xaa
         35                  40                  45
Xaa Xaa Xaa Xaa Xaa Xaa Xaa Xaa Xaa Xaa Xaa Xaa Xaa Cys Cys Xaa Xaa
     50                  55                  60
Xaa Xaa Xaa Xaa Xaa Xaa Xaa Xaa Xaa Xaa Xaa Xaa Xaa Xaa Xaa Xaa
 65                  70                  75                  80
Xaa Xaa Xaa Xaa Xaa Xaa Xaa Xaa Xaa Xaa Xaa Xaa Xaa Cys Xaa Cys
             85                  90                  95
Xaa
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ3
            /note= "WHEREIN EACH XAA IS INDEPENDENTLY SELECTED
            FROM A GROUP OF ONE OR MORE SPECIFIED AMINO ACIDS
            AS DEFINED IN THE SPECIFICATION."

(xi) SEQUENCE DESCRIPTION: SEQ ID NO:3:

```
Leu Tyr Val Xaa Phe Xaa Xaa Xaa Gly Trp Xaa Xaa Trp Xaa Xaa Ala
 1               5                  10                  15
Pro Xaa Gly Xaa Xaa Ala Xaa Tyr Cys Xaa Gly Xaa Cys Xaa Xaa Pro
             20                  25                  30
Xaa Xaa Xaa Xaa Xaa Xaa Xaa Xaa Asn His Ala Xaa Xaa Xaa Xaa Leu
         35                  40                  45
Xaa Xaa Xaa Xaa Xaa Xaa Xaa Xaa Xaa Xaa Xaa Cys Cys Xaa Pro
     50                  55                  60
Xaa Xaa Xaa Xaa Xaa Xaa Xaa Xaa Leu Xaa Xaa Xaa Xaa Xaa Xaa Xaa
 65                  70                  75                  80
Val Xaa Leu Xaa Xaa Xaa Xaa Xaa Met Xaa Val Xaa Xaa Cys Gly Cys
             85                  90                  95
```

Xaa (2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ4
            /note= "WHEREIN EACH XAA IS INDEPENDENTLY SELECTED
            FROM A GROUP OF ONE OR MORE SPECIFIED AMINO ACIDS
            AS DEFINED IN THE SPECIFICATION."

(xi) SEQUENCE DESCRIPTION: SEQ ID NO:4:

```
Cys Xaa Xaa Xaa Xaa Leu Tyr Val Xaa Phe Xaa Xaa Xaa Gly Trp Xaa
1               5                   10                  15

Xaa Trp Xaa Xaa Ala Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Leu Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Gly Cys Xaa
            100
```

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens
        (F) TISSUE TYPE: HIPPOCAMPUS (ix) FEATURE:
        (A) NAME/KEY: Protein
        (B) LOCATION: 1..139
        (D) OTHER INFORMATION: /label= hOP1-MATURE (xi) SEQUENCE DESCRIPTION: SEQ ID NO:5:

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
```

```
65                  70                  75                  80
Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

(2) INFORMATION FOR SEQ ID NO:6:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE
        (F) TISSUE TYPE: EMBRYO (ix) FEATURE:
        (A) NAME/KEY: Protein
        (B) LOCATION: 1..139
        (D) OTHER INFORMATION: /label= MOP1-MATURE (xi) SEQUENCE DESCRIPTION: SEQ ID NO:6:

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
                20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

(2) INFORMATION FOR SEQ ID NO:7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: HIPPOCAMPUS (ix) FEATURE:

(A) NAME/KEY: Protein
            (B) LOCATION: 1..139
            (D) OTHER INFORMATION: /label= HOP2-MATURE (xi) SEQUENCE DESCRIPTION: SEQ ID NO:7:

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
                20                  25                  30

His Gly Arg Gln Val Cys Arg Arg His Glu Leu Tyr Val Ser Phe Gln
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
                100                 105                 110

Ser Val Leu Tyr Tyr Asp Ser Ser Asn Asn Val Ile Leu Arg Lys His
            115                 120                 125

Arg Asn Met Val Val Lys Ala Cys Gly Cys His
        130                 135

(2) INFORMATION FOR SEQ ID NO:8:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE
        (F) TISSUE TYPE: EMBRYO (ix) FEATURE:
        (A) NAME/KEY: Protein
        (B) LOCATION: 1..139
        (D) OTHER INFORMATION: /label= MOP2-MATURE (xi) SEQUENCE DESCRIPTION: SEQ ID NO:8:

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
                20                  25                  30

Arg Gly Arg Glu Val Cys Arg Arg His Glu Leu Tyr Val Ser Phe Arg
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
                100                 105                 110

Ser Val Leu Tyr Tyr Asp Ser Ser Asn Asn Val Ile Leu Arg Lys His
            115                 120                 125

```
Arg Asn Met Val Val Lys Ala Cys Gly Cys His
    130                 135
```

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: bovinae (ix) FEATURE:
        (A) NAME/KEY: Protein
        (B) LOCATION: 1..101
        (D) OTHER INFORMATION: /label= CBMP-2A-FX (xi) SEQUENCE DESCRIPTION: SEQ ID NO:9:

```
Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
                20                  25                  30

Glu Cys Pro Phe Pro Leu Ala Asp His Leu Asn Ser Thr Asn His Ala
            35                  40                  45

Ile Val Gln Thr Leu Val Asn Ser Val Asn Ser Lys Ile Pro Lys Ala
        50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100
```

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: hippocampus (ix) FEATURE:
        (A) NAME/KEY: Protein
        (B) LOCATION: 1..101
        (D) OTHER INFORMATION: /label= CBMP-2B-FX (xi) SEQUENCE DESCRIPTION: SEQ ID NO:10:

```
Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
                20                  25                  30

Asp Cys Pro Phe Pro Leu Ala Asp His Leu Asn Ser Thr Asn His Ala
            35                  40                  45

Ile Val Gln Thr Leu Val Asn Ser Val Asn Ser Ser Ile Pro Lys Ala
        50                  55                  60
```

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100

(2) INFORMATION FOR SEQ ID NO:11:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: DROSOPHILA MELANOGASTER (ix) FEATURE:
        (A) NAME/KEY: Protein
        (B) LOCATION: 1..101
        (D) OTHER INFORMATION: /label= DPP-FX (xi) SEQUENCE DESCRIPTION: SEQ ID NO:11:

Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
                20                  25                  30

Lys Cys Pro Phe Pro Leu Ala Asp His Phe Asn Ser Thr Asn His Ala
            35                  40                  45

Val Val Gln Thr Leu Val Asn Asn Asn Pro Gly Lys Val Pro Lys
        50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: XENOPUS (ix) FEATURE:
        (A) NAME/KEY: Protein
        (B) LOCATION: 1..102
        (D) OTHER INFORMATION: /label= VGL-FX (xi) SEQUENCE DESCRIPTION: SEQ ID NO:12:

Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
                20                  25                  30

Glu Cys Pro Tyr Pro Leu Thr Glu Ile Leu Asn Gly Ser Asn His Ala

```
                35                  40                  45
Ile Leu Gln Thr Leu Val His Ser Ile Glu Pro Glu Asp Ile Pro Leu
            50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100
```

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE (ix) FEATURE:
        (A) NAME/KEY: Protein
        (B) LOCATION: 1..102
        (D) OTHER INFORMATION: /label= VGR-1-FX (xi) SEQUENCE DESCRIPTION: SEQ ID NO:13:

```
Cys Lys Lys His Glu Leu Tyr Val Ser Phe Gln Asp Val Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Val Met Asn Pro Glu Tyr Val Pro Lys
    50                  55                  60

Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100
```

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens
        (F) TISSUE TYPE: brain (ix) FEATURE:
        (A) NAME/KEY: Protein
        (B) LOCATION: 1..106
        (D) OTHER INFORMATION: /note= "GDF-1 (fx)"

(xi) SEQUENCE DESCRIPTION: SEQ ID NO:14:

| Cys | Arg | Ala | Arg | Arg | Leu | Tyr | Val | Ser | Phe | Arg | Glu | Val | Gly | Trp | His |
|---|---|---|---|---|---|---|---|---|---|---|---|---|---|---|---|
| 1 | | | | 5 | | | | | 10 | | | | | 15 | |

| Arg | Trp | Val | Ile | Ala | Pro | Arg | Gly | Phe | Leu | Ala | Asn | Tyr | Cys | Gln | Gly |
|---|---|---|---|---|---|---|---|---|---|---|---|---|---|---|---|
| | | | 20 | | | | | 25 | | | | | 30 | | |

| Gln | Cys | Ala | Leu | Pro | Val | Ala | Leu | Ser | Gly | Ser | Gly | Gly | Pro | Pro | Ala |
|---|---|---|---|---|---|---|---|---|---|---|---|---|---|---|---|
| | | 35 | | | | | 40 | | | | | 45 | | | |

| Leu | Asn | His | Ala | Val | Leu | Arg | Ala | Leu | Met | His | Ala | Ala | Ala | Pro | Gly |
|---|---|---|---|---|---|---|---|---|---|---|---|---|---|---|---|
| | 50 | | | | | 55 | | | | | 60 | | | | |

| Ala | Ala | Asp | Leu | Pro | Cys | Cys | Val | Pro | Ala | Arg | Leu | Ser | Pro | Ile | Ser |
|---|---|---|---|---|---|---|---|---|---|---|---|---|---|---|---|
| 65 | | | | | 70 | | | | | 75 | | | | | 80 |

| Val | Leu | Phe | Phe | Asp | Asn | Ser | Asp | Asn | Val | Val | Leu | Arg | Gln | Tyr | Glu |
|---|---|---|---|---|---|---|---|---|---|---|---|---|---|---|---|
| | | | | 85 | | | | | 90 | | | | | 95 | |

| Asp | Met | Val | Val | Asp | Glu | Cys | Gly | Cys | Arg |
|---|---|---|---|---|---|---|---|---|---|
| | | | 100 | | | | 105 | | |

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

| Cys | Xaa | Xaa | Xaa | Xaa |
|---|---|---|---|---|
| 1 | | | | 5 |

(2) INFORMATION FOR SEQ ID NO:16:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS
        (F) TISSUE TYPE: HIPPOCAMPUS (ix) FEATURE:
        (A) NAME/KEY: CDS
        (B) LOCATION: 49..1341
        (C) IDENTIFICATION METHOD: experimental
        (D) OTHER INFORMATION: /function= "OSTEOGENIC PROTEIN"
            /product= "OP1"
            /evidence= EXPERIMENTAL
            /standard_name= "OP1"

(xi) SEQUENCE DESCRIPTION: SEQ ID NO:16:

```
GGTGCGGGCC CGGAGCCCGG AGCCCGGGTA GCGCGTAGAG CCGGCGCG ATG CAC GTG      57
                                                     Met His Val
                                                      1

CGC TCA CTG CGA GCT GCG GCG CCG CAC AGC TTC GTG GCG CTC TGG GCA      105
Arg Ser Leu Arg Ala Ala Ala Pro His Ser Phe Val Ala Leu Trp Ala
         5                  10                  15

CCC CTG TTC CTG CTG CGC TCC GCC CTG GCC GAC TTC AGC CTG GAC AAC      153
```

```
Pro Leu Phe Leu Leu Arg Ser Ala Leu Ala Asp Phe Ser Leu Asp Asn
 20              25                  30                  35

GAG GTG CAC TCG AGC TTC ATC CAC CGG CGC CTC CGC AGC CAG GAG CGG    201
Glu Val His Ser Ser Phe Ile His Arg Arg Leu Arg Ser Gln Glu Arg
             40                  45                  50

CGG GAG ATG CAG CGC GAG ATC CTC TCC ATT TTG GGC TTG CCC CAC CGC    249
Arg Glu Met Gln Arg Glu Ile Leu Ser Ile Leu Gly Leu Pro His Arg
         55                  60                  65

CCG CGC CCG CAC CTC CAG GGC AAG CAC AAC TCG GCA CCC ATG TTC ATG    297
Pro Arg Pro His Leu Gln Gly Lys His Asn Ser Ala Pro Met Phe Met
     70                  75                  80

CTG GAC CTG TAC AAC GCC ATG GCG GTG GAG GAG GGC GGC GGG CCC GGC    345
Leu Asp Leu Tyr Asn Ala Met Ala Val Glu Glu Gly Gly Gly Pro Gly
 85                  90                  95

GGC CAG GGC TTC TCC TAC CCC TAC AAG GCC GTC TTC AGT ACC CAG GGC    393
Gly Gln Gly Phe Ser Tyr Pro Tyr Lys Ala Val Phe Ser Thr Gln Gly
100             105                 110                 115

CCC CCT CTG GCC AGC CTG CAA GAT AGC CAT TTC CTC ACC GAC GCC GAC    441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC    489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC    537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC    585
Pro Glu Gly Glu Ala Val Thr Ala Ala Glu Phe Arg Ile Tyr Lys Asp
    165                 170                 175

TAC ATC CGG GAA CGC TTC GAC AAT GAG ACG TTC CGG ATC AGC GTT TAT    633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC    681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC    729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG    777
Ile Thr Ala Thr Ser Asn His Trp Val Val Asn Pro Arg His Asn Leu
        230                 235                 240

GGC CTG CAG CTC TCG GTG GAG ACG CTG GAT GGG CAG AGC ATC AAC CCC    825
Gly Leu Gln Leu Ser Val Glu Thr Leu Asp Gly Gln Ser Ile Asn Pro
    245                 250                 255

AAG TTG GCG GGC CTG ATT GGG CGG CAC GGG CCC CAG AAC AAG CAG CCC    873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC    921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC    969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC    1017
Lys Asn Gln Glu Ala Leu Arg Met Ala Asn Val Ala Glu Asn Ser Ser
        310                 315                 320

AGC GAC CAG AGG CAG GCC TGT AAG AAG CAC GAG CTG TAT GTC AGC TTC    1065
Ser Asp Gln Arg Gln Ala Cys Lys Lys His Glu Leu Tyr Val Ser Phe
    325                 330                 335
```

```
CGA GAC CTG GGC TGG CAG GAC TGG ATC ATC GCG CCT GAA GGC TAC GCC      1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG      1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC      1209
Asn Ala Thr Asn His Ala Ile Val Gln Thr Leu Val His Phe Ile Asn
            375                 380                 385

CCG GAA ACG GTG CCC AAG CCC TGT TGT GCG CCC ACG CAG CTC AAT GCC      1257
Pro Glu Thr Val Pro Lys Pro Cys Cys Ala Pro Thr Gln Leu Asn Ala
        390                 395                 400

ATC TCC GTC CTC TAC TTC GAT GAC AGC TCC AAC GTC ATC CTG AAG AAA      1305
Ile Ser Val Leu Tyr Phe Asp Asp Ser Ser Asn Val Ile Leu Lys Lys
    405                 410                 415

TAC AGA AAC ATG GTG GTC CGG GCC TGT GGC TGC CAC TAGCTCCTCC           1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG    1411

GAACCAGCAG ACCAACTGCC TTTTGTGAGA CCTTCCCCTC CCTATCCCCA ACTTTAAAGG    1471

TGTGAGAGTA TTAGGAAACA TGAGCAGCAT ATGGCTTTTG ATCAGTTTTT CAGTGGCAGC    1531

ATCCAATGAA CAAGATCCTA CAAGCTGTGC AGGCAAAACC TAGCAGGAAA AAAAAACAAC    1591

GCATAAAGAA AAATGGCCGG GCCAGGTCAT TGGCTGGGAA GTCTCAGCCA TGCACGGACT    1651

CGTTTCCAGA GGTAATTATG AGCGCCTACC AGCCAGGCCA CCCAGCCGTG GGAGGAAGGG    1711

GGCGTGGCAA GGGGTGGGCA CATTGGTGTC TGTGCGAAAG GAAAATTGAC CCGGAAGTTC    1771

CTGTAATAAA TGTCACAATA AAACGAATGA ATGAAAAAAA AAAAAAAAA A             1822

(2) INFORMATION FOR SEQ ID NO:17:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:17:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140
```

```
Glu Phe Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln His Leu Gly Arg Glu Ser Asp Leu
                195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
                370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

(2) INFORMATION FOR SEQ ID NO:18:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: MURIDAE
        (F) TISSUE TYPE: EMBRYO (ix) FEATURE:
        (A) NAME/KEY: CDS
        (B) LOCATION: 104..1393
        (D) OTHER INFORMATION: /function= "OSTEOGENIC PROTEIN"
            /product= "MOP1"
            /note= "MOP1 (CDNA)"
```

(xi) SEQUENCE DESCRIPTION: SEQ ID NO:18:

```
CTGCAGCAAG TGACCTCGGG TCGTGGACCG CTGCCCTGCC CCCTCCGCTG CCACCTGGGG          60

CGGCGCGGGC CCGGTGCCCC GGATCGCGCG TAGAGCCGGC GCG ATG CAC GTG CGC          115
                                                Met His Val Arg
                                                  1

TCG CTG CGC GCT GCG GCG CCA CAC AGC TTC GTG GCG CTC TGG GCG CCT          163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG          211
Leu Phe Leu Leu Arg Ser Ala Leu Ala Asp Phe Ser Leu Asp Asn Glu
             25                  30                  35

GTG CAC TCC AGC TTC ATC CAC CGG CGC CTC CGC AGC CAG GAG CGG CGG          259
Val His Ser Ser Phe Ile His Arg Arg Leu Arg Ser Gln Glu Arg Arg
         40                  45                  50

GAG ATG CAG CGG GAG ATC CTG TCC ATC TTA GGG TTG CCC CAT CGC CCG          307
Glu Met Gln Arg Glu Ile Leu Ser Ile Leu Gly Leu Pro His Arg Pro
     55                  60                  65

CGC CCG CAC CTC CAG GGA AAG CAT AAT TCG GCG CCC ATG TTC ATG TTG          355
Arg Pro His Leu Gln Gly Lys His Asn Ser Ala Pro Met Phe Met Leu
 70                  75                  80

GAC CTG TAC AAC GCC ATG GCG GTG GAG GAG AGC GGG CCG GAC GGA CAG          403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT          451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC          499
Leu Ala Ser Leu Gln Asp Ser His Phe Leu Thr Asp Ala Asp Met Val
        120                 125                 130

ATG AGC TTC GTC AAC CTA GTG GAA CAT GAC AAA GAA TTC TTC CAC CCT          547
Met Ser Phe Val Asn Leu Val Glu His Asp Lys Glu Phe Phe His Pro
            135                 140                 145

CGA TAC CAC CAT CGG GAG TTC CGG TTT GAT CTT TCC AAG ATC CCC GAG          595
Arg Tyr His His Arg Glu Phe Arg Phe Asp Leu Ser Lys Ile Pro Glu
        150                 155                 160

GGC GAA CGG GTG ACC GCA GCC GAA TTC AGG ATC TAT AAG GAC TAC ATC          643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG          691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC          739
Leu Gln Glu His Ser Gly Arg Glu Ser Asp Leu Phe Leu Leu Asp Ser
        200                 205                 210

CGC ACC ATC TGG GCT TCT GAG GAG GGC TGG TTG GTG TTT GAT ATC ACA          787
Arg Thr Ile Trp Ala Ser Glu Glu Gly Trp Leu Val Phe Asp Ile Thr
            215                 220                 225

GCC ACC AGC AAC CAC TGG GTG GTC AAC CCT CGG CAC AAC CTG GGC TTA          835
Ala Thr Ser Asn His Trp Val Val Asn Pro Arg His Asn Leu Gly Leu
        230                 235                 240

CAG CTC TCT GTG GAG ACC CTG GAT GGG CAG AGC ATC AAC CCC AAG TTG          883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG          931
Ala Gly Leu Ile Gly Arg His Gly Pro Gln Asn Lys Gln Pro Phe Met
                265                 270                 275

GTG GCC TTC TTC AAG GCC ACG GAA GTC CAT CTC CGT AGT ATC CGG TCC          979
Val Ala Phe Phe Lys Ala Thr Glu Val His Leu Arg Ser Ile Arg Ser
```

```
                     280                285                 290
ACG GGG GGC AAG CAG CGC AGC CAG AAT CGC TCC AAG ACG CCA AAG AAC     1027
Thr Gly Gly Lys Gln Arg Ser Gln Asn Arg Ser Lys Thr Pro Lys Asn
            295                 300                 305

CAA GAG GCC CTG AGG ATG GCC AGT GTG GCA GAA AAC AGC AGC AGT GAC     1075
Gln Glu Ala Leu Arg Met Ala Ser Val Ala Glu Asn Ser Ser Ser Asp
            310                 315                 320

CAG AGG CAG GCC TGC AAG AAA CAT GAG CTG TAC GTC AGC TTC CGA GAC     1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC     1171
Leu Gly Trp Gln Asp Trp Ile Ile Ala Pro Glu Gly Tyr Ala Ala Tyr
            345                 350                 355

TAC TGT GAG GGA GAG TGC GCC TTC CCT CTG AAC TCC TAC ATG AAC GCC     1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC     1267
Thr Asn His Ala Ile Val Gln Thr Leu Val His Phe Ile Asn Pro Asp
            375                 380                 385

ACA GTA CCC AAG CCC TGC TGT GCG CCC ACC CAG CTC AAC GCC ATC TCT     1315
Thr Val Pro Lys Pro Cys Cys Ala Pro Thr Gln Leu Asn Ala Ile Ser
            390                 395                 400

GTC CTC TAC TTC GAC GAC AGC TCT AAT GTC GAC CTG AAG AAG TAC AGA     1363
Val Leu Tyr Phe Asp Asp Ser Ser Asn Val Asp Leu Lys Lys Tyr Arg
405                 410                 415                 420

AAC ATG GTG GTC CGG GCC TGT GGC TGC CAC TAGCTCTTCC TGAGACCCTG       1413
Asn Met Val Val Arg Ala Cys Gly Cys His
            425                 430

ACCTTTGCGG GGCCACACCT TTCCAAATCT TCGATGTCTC ACCATCTAAG TCTCTCACTG   1473

CCCACCTTGG CGAGGAGAAC AGACCAACCT CTCCTGAGCC TTCCCTCACC TCCCAACCGG   1533

AAGCATGTAA GGGTTCCAGA AACCTGAGCG TGCAGCAGCT GATGAGCGCC CTTTCCTTCT   1593

GGCACGTGAC GGACAAGATC CTACCAGCTA CCACAGCAAA CGCCTAAGAG CAGGAAAAAT   1653

GTCTGCCAGG AAAGTGTCCA GTGTCCACAT GGCCCCTGGC GCTCTGAGTC TTTGAGGAGT   1713

AATCGCAAGC CTCGTTCAGC TGCAGCAGAA GGAAGGGCTT AGCCAGGGTG GGCGCTGGCG   1773

TCTGTGTTGA AGGGAAACCA AGCAGAAGCC ACTGTAATGA TATGTCACAA TAAAACCCAT   1833

GAATGAAAAA AAAAAAAAAA AAAAAAAAAA AAAAGAATTC                         1873

(2) INFORMATION FOR SEQ ID NO:19:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:19:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
```

```
                65                  70                  75                  80
        Met Phe Met Leu Asp Leu Tyr Asn Ala Met Ala Val Glu Glu Ser Gly
                            85                  90                  95

Pro Asp Gly Gln Gly Phe Ser Tyr Pro Tyr Lys Ala Val Phe Ser Thr
                        100                 105                 110

Gln Gly Pro Pro Leu Ala Ser Leu Gln Asp Ser His Phe Leu Thr Asp
                    115                 120                 125

Ala Asp Met Val Met Ser Phe Val Asn Leu Val Glu His Asp Lys Glu
                130                 135                 140

Phe Phe His Pro Arg Tyr His His Arg Glu Phe Arg Phe Asp Leu Ser
        145                 150                 155                 160

Lys Ile Pro Glu Gly Glu Arg Val Thr Ala Ala Glu Phe Arg Ile Tyr
                        165                 170                 175

Lys Asp Tyr Ile Arg Glu Arg Phe Asp Asn Glu Thr Phe Gln Ile Thr
                    180                 185                 190

Val Tyr Gln Val Leu Gln Glu His Ser Gly Arg Glu Ser Asp Leu Phe
                195                 200                 205

Leu Leu Asp Ser Arg Thr Ile Trp Ala Ser Glu Glu Gly Trp Leu Val
            210                 215                 220

Phe Asp Ile Thr Ala Thr Ser Asn His Trp Val Val Asn Pro Arg His
        225                 230                 235                 240

Asn Leu Gly Leu Gln Leu Ser Val Glu Thr Leu Asp Gly Gln Ser Ile
                        245                 250                 255

Asn Pro Lys Leu Ala Gly Leu Ile Gly Arg His Gly Pro Gln Asn Lys
                    260                 265                 270

Gln Pro Phe Met Val Ala Phe Phe Lys Ala Thr Glu Val His Leu Arg
                275                 280                 285

Ser Ile Arg Ser Thr Gly Gly Lys Gln Arg Ser Gln Asn Arg Ser Lys
            290                 295                 300

Thr Pro Lys Asn Gln Glu Ala Leu Arg Met Ala Ser Val Ala Glu Asn
        305                 310                 315                 320

Ser Ser Ser Asp Gln Arg Gln Ala Cys Lys Lys His Glu Leu Tyr Val
                        325                 330                 335

Ser Phe Arg Asp Leu Gly Trp Gln Asp Trp Ile Ile Ala Pro Glu Gly
                    340                 345                 350

Tyr Ala Ala Tyr Tyr Cys Glu Gly Glu Cys Ala Phe Pro Leu Asn Ser
                355                 360                 365

Tyr Met Asn Ala Thr Asn His Ala Ile Val Gln Thr Leu Val His Phe
            370                 375                 380

Ile Asn Pro Asp Thr Val Pro Lys Pro Cys Cys Ala Pro Thr Gln Leu
        385                 390                 395                 400

Asn Ala Ile Ser Val Leu Tyr Phe Asp Asp Ser Ser Asn Val Asp Leu
                        405                 410                 415

Lys Lys Tyr Arg Asn Met Val Val Arg Ala Cys Gly Cys His
                    420                 425                 430

(2) INFORMATION FOR SEQ ID NO:20:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA
```

-continued (vi) ORIGINAL SOURCE:
    (A) ORGANISM: Homo sapiens
    (F) TISSUE TYPE: HIPPOCAMPUS (ix) FEATURE:
    (A) NAME/KEY: CDS
    (B) LOCATION: 490..1696
    (D) OTHER INFORMATION: /function= "OSTEOGENIC PROTEIN"
        /product= "hOP2-PP"
        /note= "hOP2 (cDNA)"

(xi) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA         60

GGGCTGGAGG GCTCCCTATG AGTGGCGGAG ACGGCCCAGG AGGCGCTGGA GCAACAGCTC        120

CCACACCGCA CCAAGCGGTG GCTGCAGGAG CTCGCCCATC GCCCCTGCGC TGCTCGGACC        180

GCGGCCACAG CCGGACTGGC GGGTACGGCG GCGACAGAGG CATTGGCCGA GAGTCCCAGT        240

CCGCAGAGTA GCCCCGGCCT CGAGGCGGTG GCGTCCCGGT CCTCTCCGTC CAGGAGCCAG        300

GACAGGTGTC GCGCGGCGGG GCTCCAGGGA CCGCGCCTGA GGCCGGCTGC CCGCCCGTCC        360

CGCCCCGCCC CGCCGCCCGC CGCCCGCCGA GCCCAGCCTC CTTGCCGTCG GGGCGTCCCC        420

AGGCCCTGGG TCGGCCGCGG AGCCGATGCG CGCCCGCTGA GCGCCCCAGC TGAGCGCCCC        480
```

| | | | | | | | | | | | | | | | | |
|---|---|---|---|---|---|---|---|---|---|---|---|---|---|---|---|---|
| CGGCCTGCC | ATG | ACC | GCG | CTC | CCC | GGC | CCG | CTC | TGG | CTC | CTG | GGC | CTG | | | 528 |
| | Met | Thr | Ala | Leu | Pro | Gly | Pro | Leu | Trp | Leu | Leu | Gly | Leu | | | |
| | 1 | | | | 5 | | | | | 10 | | | | | | |

| GCG | CTA | TGC | GCG | CTG | GGC | GGG | GGC | GGC | CCC | GGC | CTG | CGA | CCC | CCG | CCC | 576 |
|---|---|---|---|---|---|---|---|---|---|---|---|---|---|---|---|---|
| Ala | Leu | Cys | Ala | Leu | Gly | Gly | Gly | Gly | Pro | Gly | Leu | Arg | Pro | Pro | Pro | |
| 15 | | | | | 20 | | | | | 25 | | | | | | |

| GGC | TGT | CCC | CAG | CGA | CGT | CTG | GGC | GCG | CGC | GAG | CGC | CGG | GAC | GTG | CAG | 624 |
|---|---|---|---|---|---|---|---|---|---|---|---|---|---|---|---|---|
| Gly | Cys | Pro | Gln | Arg | Arg | Leu | Gly | Ala | Arg | Glu | Arg | Arg | Asp | Val | Gln | |
| 30 | | | | 35 | | | | | 40 | | | | | 45 | | |

| CGC | GAG | ATC | CTG | GCG | GTG | CTC | GGG | CTG | CCT | GGG | CGG | CCC | CGG | CCC | CGC | 672 |
|---|---|---|---|---|---|---|---|---|---|---|---|---|---|---|---|---|
| Arg | Glu | Ile | Leu | Ala | Val | Leu | Gly | Leu | Pro | Gly | Arg | Pro | Arg | Pro | Arg | |
| | | | 50 | | | | | 55 | | | | | 60 | | | |

| GCG | CCA | CCC | GCC | GCC | TCC | CGG | CTG | CCC | GCG | TCC | GCG | CCG | CTC | TTC | ATG | 720 |
|---|---|---|---|---|---|---|---|---|---|---|---|---|---|---|---|---|
| Ala | Pro | Pro | Ala | Ala | Ser | Arg | Leu | Pro | Ala | Ser | Ala | Pro | Leu | Phe | Met | |
| | | 65 | | | | | 70 | | | | | 75 | | | | |

| CTG | GAC | CTG | TAC | CAC | GCC | ATG | GCC | GGC | GAC | GAC | GAC | GAG | GAC | GGC | GCG | 768 |
|---|---|---|---|---|---|---|---|---|---|---|---|---|---|---|---|---|
| Leu | Asp | Leu | Tyr | His | Ala | Met | Ala | Gly | Asp | Asp | Asp | Glu | Asp | Gly | Ala | |
| | 80 | | | | | 85 | | | | | 90 | | | | | |

| CCC | GCG | GAG | CGG | CGC | CTG | GGC | CGC | GCC | GAC | CTG | GTC | ATG | AGC | TTC | GTT | 816 |
|---|---|---|---|---|---|---|---|---|---|---|---|---|---|---|---|---|
| Pro | Ala | Glu | Arg | Arg | Leu | Gly | Arg | Ala | Asp | Leu | Val | Met | Ser | Phe | Val | |
| 95 | | | | | 100 | | | | | 105 | | | | | | |

| AAC | ATG | GTG | GAG | CGA | GAC | CGT | GCC | CTG | GGC | CAC | CAG | GAG | CCC | CAT | TGG | 864 |
|---|---|---|---|---|---|---|---|---|---|---|---|---|---|---|---|---|
| Asn | Met | Val | Glu | Arg | Asp | Arg | Ala | Leu | Gly | His | Gln | Glu | Pro | His | Trp | |
| 110 | | | | 115 | | | | | 120 | | | | | 125 | | |

| AAG | GAG | TTC | CGC | TTT | GAC | CTG | ACC | CAG | ATC | CCG | GCT | GGG | GAG | GCG | GTC | 912 |
|---|---|---|---|---|---|---|---|---|---|---|---|---|---|---|---|---|
| Lys | Glu | Phe | Arg | Phe | Asp | Leu | Thr | Gln | Ile | Pro | Ala | Gly | Glu | Ala | Val | |
| | | | 130 | | | | | 135 | | | | | 140 | | | |

| ACA | GCT | GCG | GAG | TTC | CGG | ATT | TAC | AAG | GTG | CCC | AGC | ATC | CAC | CTG | CTC | 960 |
|---|---|---|---|---|---|---|---|---|---|---|---|---|---|---|---|---|
| Thr | Ala | Ala | Glu | Phe | Arg | Ile | Tyr | Lys | Val | Pro | Ser | Ile | His | Leu | Leu | |
| | | 145 | | | | | 150 | | | | | 155 | | | | |

| AAC | AGG | ACC | CTC | CAC | GTC | AGC | ATG | TTC | CAG | GTG | GTC | CAG | GAG | CAG | TCC | 1008 |
|---|---|---|---|---|---|---|---|---|---|---|---|---|---|---|---|---|
| Asn | Arg | Thr | Leu | His | Val | Ser | Met | Phe | Gln | Val | Val | Gln | Glu | Gln | Ser | |
| | 160 | | | | | 165 | | | | | 170 | | | | | |

| AAC | AGG | GAG | TCT | GAC | TTG | TTC | TTT | TTG | GAT | CTT | CAG | ACG | CTC | CGA | GCT | 1056 |
|---|---|---|---|---|---|---|---|---|---|---|---|---|---|---|---|---|
| Asn | Arg | Glu | Ser | Asp | Leu | Phe | Phe | Leu | Asp | Leu | Gln | Thr | Leu | Arg | Ala | |
| 175 | | | | | 180 | | | | | 185 | | | | | | |

| GGA | GAC | GAG | GGC | TGG | CTG | GTG | CTG | GAT | GTC | ACA | GCA | GCC | AGT | GAC | TGC | 1104 |
|---|---|---|---|---|---|---|---|---|---|---|---|---|---|---|---|---|
| Gly | Asp | Glu | Gly | Trp | Leu | Val | Leu | Asp | Val | Thr | Ala | Ala | Ser | Asp | Cys | |

-continued

```
           190                     195                    200                     205
TGG TTG CTG AAG CGT CAC AAG GAC CTG GGA CTC CGC CTC TAT GTG GAG           1152
Trp Leu Leu Lys Arg His Lys Asp Leu Gly Leu Arg Leu Tyr Val Glu
                    210                     215                     220

ACT GAG GAC GGG CAC AGC GTG GAT CCT GGC CTG GCC GGC CTG CTG GGT           1200
Thr Glu Asp Gly His Ser Val Asp Pro Gly Leu Ala Gly Leu Leu Gly
                225                     230                     235

CAA CGG GCC CCA CGC TCC CAA CAG CCT TTC GTG GTC ACT TTC TTC AGG           1248
Gln Arg Ala Pro Arg Ser Gln Gln Pro Phe Val Val Thr Phe Phe Arg
            240                     245                     250

GCC AGT CCG AGT CCC ATC CGC ACC CCT CGG GCA GTG AGG CCA CTG AGG           1296
Ala Ser Pro Ser Pro Ile Arg Thr Pro Arg Ala Val Arg Pro Leu Arg
        255                     260                     265

AGG AGG CAG CCG AAG AAA AGC AAC GAG CTG CCG CAG GCC AAC CGA CTC           1344
Arg Arg Gln Pro Lys Lys Ser Asn Glu Leu Pro Gln Ala Asn Arg Leu
270                     275                     280                     285

CCA GGG ATC TTT GAT GAC GTC CAC GGC TCC CAC GGC CGG CAG GTC TGC           1392
Pro Gly Ile Phe Asp Asp Val His Gly Ser His Gly Arg Gln Val Cys
                    290                     295                     300

CGT CGG CAC GAG CTC TAC GTC AGC TTC CAG GAC CTC GGC TGG CTG GAC           1440
Arg Arg His Glu Leu Tyr Val Ser Phe Gln Asp Leu Gly Trp Leu Asp
                305                     310                     315

TGG GTC ATC GCT CCC CAA GGC TAC TCG GCC TAT TAC TGT GAG GGG GAG           1488
Trp Val Ile Ala Pro Gln Gly Tyr Ser Ala Tyr Tyr Cys Glu Gly Glu
            320                     325                     330

TGC TCC TTC CCA CTG GAC TCC TGC ATG AAT GCC ACC AAC CAC GCC ATC           1536
Cys Ser Phe Pro Leu Asp Ser Cys Met Asn Ala Thr Asn His Ala Ile
        335                     340                     345

CTG CAG TCC CTG GTG CAC CTG ATG AAG CCA AAC GCA GTC CCC AAG GCG           1584
Leu Gln Ser Leu Val His Leu Met Lys Pro Asn Ala Val Pro Lys Ala
350                     355                     360                     365

TGC TGT GCA CCC ACC AAG CTG AGC GCC ACC TCT GTG CTC TAC TAT GAC           1632
Cys Cys Ala Pro Thr Lys Leu Ser Ala Thr Ser Val Leu Tyr Tyr Asp
                    370                     375                     380

AGC AGC AAC AAC GTC ATC CTG CGC AAA GCC CGC AAC ATG GTG GTC AAG           1680
Ser Ser Asn Asn Val Ile Leu Arg Lys Ala Arg Asn Met Val Val Lys
                385                     390                     395

GCC TGC GGC TGC CAC T GAGTCAGCCC GCCCAGCCCT ACTGCAG                       1723
Ala Cys Gly Cys His
            400
```

(2) INFORMATION FOR SEQ ID NO:21:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:21:

```
Met Thr Ala Leu Pro Gly Pro Leu Trp Leu Leu Gly Leu Ala Leu Cys
  1               5                  10                  15

Ala Leu Gly Gly Gly Pro Gly Leu Arg Pro Pro Gly Cys Pro
                20                  25                  30

Gln Arg Arg Leu Gly Ala Arg Glu Arg Arg Asp Val Gln Arg Glu Ile
            35                  40                  45

Leu Ala Val Leu Gly Leu Pro Gly Arg Pro Arg Pro Arg Ala Pro Pro
        50                  55                  60

Ala Ala Ser Arg Leu Pro Ala Ser Ala Pro Leu Phe Met Leu Asp Leu
```

```
                65                  70                  75                  80
Tyr His Ala Met Ala Gly Asp Asp Glu Asp Gly Ala Pro Ala Glu
                        85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
            130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
            195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
            245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
            275                 280                 285

Phe Asp Asp Val His Gly Ser His Gly Arg Gln Val Cys Arg Arg His
            290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
            325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
            355                 360                 365

Pro Thr Lys Leu Ser Ala Thr Ser Val Leu Tyr Tyr Asp Ser Ser Asn
            370                 375                 380

Asn Val Ile Leu Arg Lys Ala Arg Asn Met Val Val Lys Ala Cys Gly
385                 390                 395                 400

Cys His (2) INFORMATION FOR SEQ ID NO:22:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (vi) ORIGINAL SOURCE:
        (A) ORGANISM: MURIDAE
        (F) TISSUE TYPE: EMBRYO (ix) FEATURE:
        (A) NAME/KEY: CDS
```

(B) LOCATION: 93..1289
(D) OTHER INFORMATION: /function= "OSTEOGENIC PROTEIN"
    /product= "mOP2-PP"
    /note= "mOP2 cDNA"

(xi) SEQUENCE DESCRIPTION: SEQ ID NO:22:

```
GCCAGGCACA GGTGCGCCGT CTGGTCCTCC CCGTCTGGCG TCAGCCGAGC CCGACCAGCT          60

ACCAGTGGAT GCGCGCCGGC TGAAAGTCCG AG ATG GCT ATG CGT CCC GGG CCA          113
                                   Met Ala Met Arg Pro Gly Pro
                                    1               5

CTC TGG CTA TTG GGC CTT GCT CTG TGC GCG CTG GGA GGC GGC CAC GGT          161
Leu Trp Leu Leu Gly Leu Ala Leu Cys Ala Leu Gly Gly Gly His Gly
         10                  15                  20

CCG CGT CCC CCG CAC ACC TGT CCC CAG CGT CGC CTG GGA GCG CGC GAG          209
Pro Arg Pro Pro His Thr Cys Pro Gln Arg Arg Leu Gly Ala Arg Glu
 25                  30                  35

CGC CGC GAC ATG CAG CGT GAA ATC CTG GCG GTG CTC GGG CTA CCG GGA          257
Arg Arg Asp Met Gln Arg Glu Ile Leu Ala Val Leu Gly Leu Pro Gly
 40                  45                  50                  55

CGG CCC CGA CCC CGT GCA CAA CCC GCC GCT GCC CGG CAG CCA GCG TCC          305
Arg Pro Arg Pro Arg Ala Gln Pro Ala Ala Ala Arg Gln Pro Ala Ser
             60                  65                  70

GCG CCC CTC TTC ATG TTG GAC CTA TAC CAC GCC ATG ACC GAT GAC GAC          353
Ala Pro Leu Phe Met Leu Asp Leu Tyr His Ala Met Thr Asp Asp Asp
         75                  80                  85

GAC GGC GGG CCA CCA CAG GCT CAC TTA GGC CGT GCC GAC CTG GTC ATG          401
Asp Gly Gly Pro Pro Gln Ala His Leu Gly Arg Ala Asp Leu Val Met
         90                  95                 100

AGC TTC GTC AAC ATG GTG GAA CGC GAC CGT ACC CTG GGC TAC CAG GAG          449
Ser Phe Val Asn Met Val Glu Arg Asp Arg Thr Leu Gly Tyr Gln Glu
105                 110                 115

CCA CAC TGG AAG GAA TTC CAC TTT GAC CTA ACC CAG ATC CCT GCT GGG          497
Pro His Trp Lys Glu Phe His Phe Asp Leu Thr Gln Ile Pro Ala Gly
120                 125                 130                 135

GAG GCT GTC ACA GCT GCT GAG TTC CGG ATC TAC AAA GAA CCC AGC ACC          545
Glu Ala Val Thr Ala Ala Glu Phe Arg Ile Tyr Lys Glu Pro Ser Thr
             140                 145                 150

CAC CCG CTC AAC ACA ACC CTC CAC ATC AGC ATG TTC GAA GTG GTC CAA          593
His Pro Leu Asn Thr Thr Leu His Ile Ser Met Phe Glu Val Val Gln
             155                 160                 165

GAG CAC TCC AAC AGG GAG TCT GAC TTG TTC TTT TTG GAT CTT CAG ACG          641
Glu His Ser Asn Arg Glu Ser Asp Leu Phe Phe Leu Asp Leu Gln Thr
         170                 175                 180

CTC CGA TCT GGG GAC GAG GGC TGG CTG GTG CTG GAC ATC ACA GCA GCC          689
Leu Arg Ser Gly Asp Glu Gly Trp Leu Val Leu Asp Ile Thr Ala Ala
185                 190                 195

AGT GAC CGA TGG CTG CTG AAC CAT CAC AAG GAC CTG GGA CTC CGC CTC          737
Ser Asp Arg Trp Leu Leu Asn His His Lys Asp Leu Gly Leu Arg Leu
200                 205                 210                 215

TAT GTG GAA ACC GCG GAT GGG CAC AGC ATG GAT CCT GGC CTG GCT GGT          785
Tyr Val Glu Thr Ala Asp Gly His Ser Met Asp Pro Gly Leu Ala Gly
             220                 225                 230

CTG CTT GGA CGA CAA GCA CCA CGC TCC AGA CAG CCT TTC ATG GTA ACC          833
Leu Leu Gly Arg Gln Ala Pro Arg Ser Arg Gln Pro Phe Met Val Thr
         235                 240                 245

TTC TTC AGG GCC AGC CAG AGT CCT GTG CGG GCC CCT CGG GCA GCG AGA          881
Phe Phe Arg Ala Ser Gln Ser Pro Val Arg Ala Pro Arg Ala Ala Arg
         250                 255                 260

CCA CTG AAG AGG AGG CAG CCA AAG AAA ACG AAC GAG CTT CCG CAC CCC          929
Pro Leu Lys Arg Arg Gln Pro Lys Lys Thr Asn Glu Leu Pro His Pro
```

```
                265                 270                 275
AAC AAA CTC CCA GGG ATC TTT GAT GAT GGC CAC GGT TCC CGC GGC AGA      977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC      1025
Glu Val Cys Arg Arg His Glu Leu Tyr Val Ser Phe Arg Asp Leu Gly
                300                 305                 310

TGG CTG GAC TGG GTC ATC GCC CCC CAG GGC TAC TCT GCC TAT TAC TGT      1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC      1121
Glu Gly Glu Cys Ala Phe Pro Leu Asp Ser Cys Met Asn Ala Thr Asn
        330                 335                 340

CAT GCC ATC TTG CAG TCT CTG GTG CAC CTG ATG AAG CCA GAT GTT GTC      1169
His Ala Ile Leu Gln Ser Leu Val His Leu Met Lys Pro Asp Val Val
    345                 350                 355

CCC AAG GCA TGC TGT GCA CCC ACC AAA CTG AGT GCC ACC TCT GTG CTG      1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG      1265
Tyr Tyr Asp Ser Ser Asn Asn Val Ile Leu Arg Lys His Arg Asn Met
                380                 385                 390

GTG GTC AAG GCC TGT GGC TGC CAC TGAGGCCCCG CCCAGCATCC TGCTTCTACT      1319
Val Val Lys Ala Cys Gly Cys His
                395

ACCTTACCAT CTGGCCGGGC CCCTCTCCAG AGGCAGAAAC CCTTCTATGT TATCATAGCT    1379

CAGACAGGGG CAATGGGAGG CCCTTCACTT CCCCTGGCCA CTTCCTGCTA AAATTCTGGT    1439

CTTTCCCAGT TCCTCTGTCC TTCATGGGGT TTCGGGGCTA TCACCCCGCC CTCTCCATCC    1499

TCCTACCCCA AGCATAGACT GAATGCACAC AGCATCCCAG AGCTATGCTA ACTGAGAGGT    1559

CTGGGGTCAG CACTGAAGGC CCACATGAGG AAGACTGATC CTTGGCCATC CTCAGCCCAC    1619

AATGGCAAAT TCTGGATGGT CTAAGAAGGC CCTGGAATTC TAAACTAGAT GATCTGGGCT    1679

CTCTGCACCA TTCATTGTGG CAGTTGGGAC ATTTTTAGGT ATAACAGACA CATACACTTA    1739

GATCAATGCA TCGCTGTACT CCTTGAAATC AGAGCTAGCT TGTTAGAAAA AGAATCAGAG    1799

CCAGGTATAG CGGTGCATGT CATTAATCCC AGCGCTAAAG AGACAGAGAC AGGAGAATCT    1859

CTGTGAGTTC AAGGCCACAT AGAAAGAGCC TGTCTCGGGA GCAGGAAAAA AAAAAAAAAC    1919

GGAATTC                                                              1926

(2) INFORMATION FOR SEQ ID NO:23:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:23:

Met Ala Met Arg Pro Gly Pro Leu Trp Leu Leu Gly Leu Ala Leu Cys
1               5                   10                  15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
        50                  55                  60
```

```
Ala Ala Arg Gln Pro Ala Ser Ala Pro Leu Phe Met Leu Asp Leu Tyr
 65                  70                  75                  80

His Ala Met Thr Asp Asp Asp Gly Gly Pro Pro Gln Ala His Leu
             85                  90                  95

Gly Arg Ala Asp Leu Val Met Ser Phe Val Asn Met Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
        275                 280                 285

Gly His Gly Ser Arg Gly Arg Glu Val Cys Arg Arg His Glu Leu Tyr
290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
        355                 360                 365

Leu Ser Ala Thr Ser Val Leu Tyr Tyr Asp Ser Ser Asn Asn Val Ile
370                 375                 380

Leu Arg Lys His Arg Asn Met Val Val Lys Ala Cys Gly Cys His
385                 390                 395
```

(2) INFORMATION FOR SEQ ID NO:24:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1368

(xi) SEQUENCE DESCRIPTION: SEQ ID NO:24:

| | | | | | | | | | | | | | | | | |
|---|---|---|---|---|---|---|---|---|---|---|---|---|---|---|---|---|
| ATG | TCG | GGA | CTG | CGA | AAC | ACC | TCG | GAG | GCC | GTT | GCA | GTG | CTC | GCC | TCC | 48 |
| Met | Ser | Gly | Leu | Arg | Asn | Thr | Ser | Glu | Ala | Val | Ala | Val | Leu | Ala | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CTG | GGA | CTC | GGA | ATG | GTT | CTG | CTC | ATG | TTC | GTG | GCG | ACC | ACG | CCG | CCG | 96 |
| Leu | Gly | Leu | Gly | Met | Val | Leu | Leu | Met | Phe | Val | Ala | Thr | Thr | Pro | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| GCC | GTT | GAG | GCC | ACC | CAG | TCG | GGG | ATT | TAC | ATA | GAC | AAC | GGC | AAG | GAC | 144 |
| Ala | Val | Glu | Ala | Thr | Gln | Ser | Gly | Ile | Tyr | Ile | Asp | Asn | Gly | Lys | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| CAG | ACG | ATC | ATG | CAC | AGA | GTG | CTG | AGC | GAG | GAC | GAC | AAG | CTG | GAC | GTC | 192 |
| Gln | Thr | Ile | Met | His | Arg | Val | Leu | Ser | Glu | Asp | Asp | Lys | Leu | Asp | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| TCG | TAC | GAG | ATC | CTC | GAG | TTC | CTG | GGC | ATC | GCC | GAA | CGG | CCG | ACG | CAC | 240 |
| Ser | Tyr | Glu | Ile | Leu | Glu | Phe | Leu | Gly | Ile | Ala | Glu | Arg | Pro | Thr | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CTG | AGC | AGC | CAC | CAG | TTG | TCG | CTG | AGG | AAG | TCG | GCT | CCC | AAG | TTC | CTG | 288 |
| Leu | Ser | Ser | His | Gln | Leu | Ser | Leu | Arg | Lys | Ser | Ala | Pro | Lys | Phe | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| CTG | GAC | GTC | TAC | CAC | CGC | ATC | ACG | GCG | GAG | GAG | GGT | CTC | AGC | GAT | CAG | 336 |
| Leu | Asp | Val | Tyr | His | Arg | Ile | Thr | Ala | Glu | Glu | Gly | Leu | Ser | Asp | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| GAT | GAG | GAC | GAC | GAC | TAC | GAA | CGC | GGC | CAT | CGG | TCC | AGG | AGG | AGC | GCC | 384 |
| Asp | Glu | Asp | Asp | Asp | Tyr | Glu | Arg | Gly | His | Arg | Ser | Arg | Arg | Ser | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| GAC | CTC | GAG | GAG | GAT | GAG | GGC | GAG | CAG | CAG | AAG | AAC | TTC | ATC | ACC | GAC | 432 |
| Asp | Leu | Glu | Glu | Asp | Glu | Gly | Glu | Gln | Gln | Lys | Asn | Phe | Ile | Thr | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| CTG | GAC | AAG | CGG | GCC | ATC | GAC | GAG | AGC | GAC | ATC | ATC | ATG | ACC | TTC | CTG | 480 |
| Leu | Asp | Lys | Arg | Ala | Ile | Asp | Glu | Ser | Asp | Ile | Ile | Met | Thr | Phe | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| AAC | AAG | CGC | CAC | CAC | AAT | GTG | GAC | GAA | CTG | CGT | CAC | GAG | CAC | GGC | CGT | 528 |
| Asn | Lys | Arg | His | His | Asn | Val | Asp | Glu | Leu | Arg | His | Glu | His | Gly | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| CGC | CTG | TGG | TTC | GAC | GTC | TCC | AAC | GTG | CCC | AAC | GAC | AAC | TAC | CTG | GTG | 576 |
| Arg | Leu | Trp | Phe | Asp | Val | Ser | Asn | Val | Pro | Asn | Asp | Asn | Tyr | Leu | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ATG | GCC | GAG | CTG | CGC | ATC | TAT | CAG | AAC | GCC | AAC | GAG | GGC | AAG | TGG | CTG | 624 |
| Met | Ala | Glu | Leu | Arg | Ile | Tyr | Gln | Asn | Ala | Asn | Glu | Gly | Lys | Trp | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| ACC | GCC | AAC | AGG | GAG | TTC | ACC | ATC | ACG | GTA | TAC | GCC | ATT | GGC | ACC | GGC | 672 |
| Thr | Ala | Asn | Arg | Glu | Phe | Thr | Ile | Thr | Val | Tyr | Ala | Ile | Gly | Thr | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| ACG | CTG | GGC | CAG | CAC | ACC | ATG | GAG | CCG | CTG | TCC | TCG | GTG | AAC | ACC | ACC | 720 |
| Thr | Leu | Gly | Gln | His | Thr | Met | Glu | Pro | Leu | Ser | Ser | Val | Asn | Thr | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GGG | GAC | TAC | GTG | GGC | TGG | TTG | GAG | CTC | AAC | GTG | ACC | GAG | GGC | CTG | CAC | 768 |
| Gly | Asp | Tyr | Val | Gly | Trp | Leu | Glu | Leu | Asn | Val | Thr | Glu | Gly | Leu | His | |
| | | | | 245 | | | | | 250 | | | | | 255 | | |

| | | | | | | | | | | | | | | | | |
|---|---|---|---|---|---|---|---|---|---|---|---|---|---|---|---|---|
| GAG | TGG | CTG | GTC | AAG | TCG | AAG | GAC | AAT | CAT | GGC | ATC | TAC | ATT | GGA | GCA | 816 |
| Glu | Trp | Leu | Val | Lys | Ser | Lys | Asp | Asn | His | Gly | Ile | Tyr | Ile | Gly | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| CAC | GCT | GTC | AAC | CGA | CCC | GAC | CGC | GAG | GTG | AAG | CTG | GAC | GAC | ATT | GGA | 864 |
| His | Ala | Val | Asn | Arg | Pro | Asp | Arg | Glu | Val | Lys | Leu | Asp | Asp | Ile | Gly | |
| | | 275 | | | | | 280 | | | | | 285 | | | | |

| | | | | | | | | | | | | | | | | |
|---|---|---|---|---|---|---|---|---|---|---|---|---|---|---|---|---|
| CTG | ATC | CAC | CGC | AAG | GTG | GAC | GAC | GAG | TTC | CAG | CCC | TTC | ATG | ATC | GGC | 912 |
| Leu | Ile | His | Arg | Lys | Val | Asp | Asp | Glu | Phe | Gln | Pro | Phe | Met | Ile | Gly | |
| | 290 | | | | | 295 | | | | | 300 | | | | | |

| | | | | | | | | | | | | | | | | |
|---|---|---|---|---|---|---|---|---|---|---|---|---|---|---|---|---|
| TTC | TTC | CGC | GGA | CCG | GAG | CTG | ATC | AAG | GCG | ACG | GCC | CAC | AGC | AGC | CAC | 960 |

```
Phe Phe Arg Gly Pro Glu Leu Ile Lys Ala Thr Ala His Ser Ser His
305                 310                 315                 320

CAC AGG AGC AAG CGA AGC GCC AGC CAT CCA CGC AAG CGC AAG AAG TCG      1008
His Arg Ser Lys Arg Ser Ala Ser His Pro Arg Lys Arg Lys Lys Ser
                325                 330                 335

GTG TCG CCC AAC AAC GTG CCG CTG CTG GAA CCG ATG GAG AGC ACG CGC      1056
Val Ser Pro Asn Asn Val Pro Leu Leu Glu Pro Met Glu Ser Thr Arg
            340                 345                 350

AGC TGC CAG ATG CAG ACC CTG TAC ATA GAC TTC AAG GAT CTG GGC TGG      1104
Ser Cys Gln Met Gln Thr Leu Tyr Ile Asp Phe Lys Asp Leu Gly Trp
        355                 360                 365

CAT GAC TGG ATC ATC GCA CCA GAG GGC TAT GGC GCC TTC TAC TGC AGC      1152
His Asp Trp Ile Ile Ala Pro Glu Gly Tyr Gly Ala Phe Tyr Cys Ser
    370                 375                 380

GGC GAG TGC AAT TTC CCG CTC AAT GCG CAC ATG AAC GCC ACG AAC CAT      1200
Gly Glu Cys Asn Phe Pro Leu Asn Ala His Met Asn Ala Thr Asn His
385                 390                 395                 400

GCG ATC GTC CAG ACC CTG GTC CAC CTG CTG GAG CCC AAG AAG GTG CCC      1248
Ala Ile Val Gln Thr Leu Val His Leu Leu Glu Pro Lys Lys Val Pro
                405                 410                 415

AAG CCC TGC TGC GCT CCG ACC AGG CTG GGA GCA CTA CCC GTT CTG TAC      1296
Lys Pro Cys Cys Ala Pro Thr Arg Leu Gly Ala Leu Pro Val Leu Tyr
            420                 425                 430

CAC CTG AAC GAC GAG AAT GTG AAC CTG AAA AAG TAT AGA AAC ATG ATT      1344
His Leu Asn Asp Glu Asn Val Asn Leu Lys Lys Tyr Arg Asn Met Ile
        435                 440                 445

GTG AAA TCC TGC GGG TGC CAT TGA                                      1368
Val Lys Ser Cys Gly Cys His
    450                 455

(2) INFORMATION FOR SEQ ID NO:25:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:25:

Met Ser Gly Leu Arg Asn Thr Ser Glu Ala Val Ala Val Leu Ala Ser
1               5                   10                  15

Leu Gly Leu Gly Met Val Leu Leu Met Phe Val Ala Thr Thr Pro Pro
            20                  25                  30

Ala Val Glu Ala Thr Gln Ser Gly Ile Tyr Ile Asp Asn Gly Lys Asp
        35                  40                  45

Gln Thr Ile Met His Arg Val Leu Ser Glu Asp Asp Lys Leu Asp Val
    50                  55                  60

Ser Tyr Glu Ile Leu Glu Phe Leu Gly Ile Ala Glu Arg Pro Thr His
65                  70                  75                  80

Leu Ser Ser His Gln Leu Ser Leu Arg Lys Ser Ala Pro Lys Phe Leu
            85                  90                  95

Leu Asp Val Tyr His Arg Ile Thr Ala Glu Glu Gly Leu Ser Asp Gln
            100                 105                 110

Asp Glu Asp Asp Tyr Glu Arg Gly His Arg Ser Arg Arg Ser Ala
        115                 120                 125

Asp Leu Glu Glu Asp Glu Gly Glu Gln Gln Lys Asn Phe Ile Thr Asp
    130                 135                 140

Leu Asp Lys Arg Ala Ile Asp Glu Ser Asp Ile Ile Met Thr Phe Leu
```

```
              145                 150                 155                 160
Asn Lys Arg His His Asn Val Asp Glu Leu Arg His Glu His Gly Arg
                165                 170                 175
Arg Leu Trp Phe Asp Val Ser Asn Val Pro Asn Asp Asn Tyr Leu Val
                180                 185                 190
Met Ala Glu Leu Arg Ile Tyr Gln Asn Ala Asn Glu Gly Lys Trp Leu
                195                 200                 205
Thr Ala Asn Arg Glu Phe Thr Ile Thr Val Tyr Ala Ile Gly Thr Gly
                210                 215                 220
Thr Leu Gly Gln His Thr Met Glu Pro Leu Ser Ser Val Asn Thr Thr
225                 230                 235                 240
Gly Asp Tyr Val Gly Trp Leu Glu Leu Asn Val Thr Glu Gly Leu His
                245                 250                 255
Glu Trp Leu Val Lys Ser Lys Asp Asn His Gly Ile Tyr Ile Gly Ala
                260                 265                 270
His Ala Val Asn Arg Pro Asp Arg Glu Val Lys Leu Asp Asp Ile Gly
                275                 280                 285
Leu Ile His Arg Lys Val Asp Asp Glu Phe Gln Pro Phe Met Ile Gly
                290                 295                 300
Phe Phe Arg Gly Pro Glu Leu Ile Lys Ala Thr Ala His Ser Ser His
305                 310                 315                 320
His Arg Ser Lys Arg Ser Ala Ser His Pro Arg Lys Arg Lys Lys Ser
                325                 330                 335
Val Ser Pro Asn Asn Val Pro Leu Leu Glu Pro Met Glu Ser Thr Arg
                340                 345                 350
Ser Cys Gln Met Gln Thr Leu Tyr Ile Asp Phe Lys Asp Leu Gly Trp
                355                 360                 365
His Asp Trp Ile Ile Ala Pro Glu Gly Tyr Gly Ala Phe Tyr Cys Ser
                370                 375                 380
Gly Glu Cys Asn Phe Pro Leu Asn Ala His Met Asn Ala Thr Asn His
385                 390                 395                 400
Ala Ile Val Gln Thr Leu Val His Leu Leu Glu Pro Lys Lys Val Pro
                405                 410                 415
Lys Pro Cys Cys Ala Pro Thr Arg Leu Gly Ala Leu Pro Val Leu Tyr
                420                 425                 430
His Leu Asn Asp Glu Asn Val Asn Leu Lys Lys Tyr Arg Asn Met Ile
                435                 440                 445
Val Lys Ser Cys Gly Cys His
450                 455

(2) INFORMATION FOR SEQ ID NO:26:

(i) SEQUENCE CHARACTERISTICS:
         (A) LENGTH: 104 amino acids
         (B) TYPE: amino acid
         (C) STRANDEDNESS: single
         (D) TOPOLOGY: linear (ii) MOLECULE TYPE: protein (ix) FEATURE:
         (A) NAME/KEY: Protein
         (B) LOCATION: 1..104
         (D) OTHER INFORMATION: /note= "BMP3"

(xi) SEQUENCE DESCRIPTION: SEQ ID NO:26:

Cys Ala Arg Arg Tyr Leu Lys Val Asp Phe Ala Asp Ile Gly Trp Ser
1               5                   10                  15
```

```
Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Ala Arg Ala Val Gly Val Val Pro Gly Ile
        50                  55                  60

Pro Glu Pro Cys Cys Val Pro Glu Lys Met Ser Ser Leu Ser Ile Leu
65                  70                  75                  80

Phe Phe Asp Glu Asn Lys Asn Val Val Leu Lys Val Tyr Pro Asn Met
                    85                  90                  95

Thr Val Glu Ser Cys Ala Cys Arg
                    100
```

(2) INFORMATION FOR SEQ ID NO:27:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP5"

(xi) SEQUENCE DESCRIPTION: SEQ ID NO:27:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
        50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                    85                  90                  95

Arg Ser Cys Gly Cys His
            100
```

(2) INFORMATION FOR SEQ ID NO:28:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP6"

-continued (xi) SEQUENCE DESCRIPTION: SEQ ID NO:28:

```
Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Trp Met Val Val
                85                  90                  95

Arg Ala Cys Gly Cys His
            100
```

(2) INFORMATION FOR SEQ ID NO:29:

(i) SEQUENCE CHARACTERISTICS:
(A) LENGTH: 102 amino acids
(B) TYPE: amino acid
(D) TOPOLOGY: linear (ii) MOLECULE TYPE: protein (ix) FEATURE:
(A) NAME/KEY: Protein
(B) LOCATION: 1..102
(D) OTHER INFORMATION: /label= OPX
/note= "WHEREIN EACH XAA IS INDEPENDENTLY SELECTED FROM A GROUP OF ONE OR MORE SPECIFIED AMINO ACIDS AS DEFINED IN THE SPECIFICATION (SECTION II.B.2.)"

(xi) SEQUENCE DESCRIPTION: SEQ ID NO:29:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

(2) INFORMATION FOR SEQ ID NO:30:

(i) SEQUENCE CHARACTERISTICS:
(A) LENGTH: 97 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..97

(D) OTHER INFORMATION: /label= GENERIC-SEQ5
                /note= "WHEREIN EACH XAA IS INDEPENDENTLY SELECTED
                FROM A GROUP OF ONE OR MORE SPECIFIED AMINO ACIDS
                AS DEFINED IN THE SPECIFICATION."

(xi) SEQUENCE DESCRIPTION: SEQ ID NO:30:

Leu Xaa Xaa Xaa Phe Xaa Xaa Xaa Gly Trp Xaa Xaa Trp Xaa Xaa Xaa
1               5                   10                  15

Pro Xaa Xaa Xaa Xaa Ala Xaa Tyr Cys Xaa Gly Xaa Cys Xaa Xaa Pro
                20                  25                  30

Xaa Xaa Xaa Xaa Xaa Xaa Xaa Xaa Asn His Ala Xaa Xaa Xaa Xaa Xaa
            35                  40                  45

Xaa Xaa Xaa Xaa Xaa Xaa Xaa Xaa Xaa Xaa Xaa Cys Cys Xaa Pro
        50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95

Xaa (2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ6
            /note= "WHEREIN EACH XAA IS INDEPENDENTLY SELECTED
            FROM A GROUP OF ONE OR MORE SPECIFIED AMINO ACIDS
            AS DEFINED IN THE SPECIFICATION. "

(xi) SEQUENCE DESCRIPTION: SEQ ID NO:31:

Cys Xaa Xaa Xaa Xaa Leu Xaa Xaa Xaa Phe Xaa Xaa Xaa Gly Trp Xaa
1               5                   10                  15

Xaa Trp Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100

(2) INFORMATION FOR SEQ ID NO:32:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: HOMO SAPIENS
    (F) TISSUE TYPE: BRAIN (ix) FEATURE:
    (A) NAME/KEY: CDS (B) LOCATION: 84..1199
    (D) OTHER INFORMATION: /product= "GDF-1"
        /note= "GDF-1 CDNA"

(xi) SEQUENCE DESCRIPTION: SEQ ID NO:32:

```
GGGGACACCG GCCCCGCCCT CAGCCCACTG GTCCCGGGCC GCCGCGGACC CTGCGCACTC       60

TCTGGTCATC GCCTGGGAGG AAG ATG CCA CCG CCG CAG CAA GGT CCC TGC          110
                         Met Pro Pro Pro Gln Gln Gly Pro Cys
                         1               5

GGC CAC CAC CTC CTC CTC CTC CTG GCC CTG CTG CTG CCC TCG CTG CCC       158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG       206
Leu Thr Arg Ala Pro Val Pro Pro Gly Pro Ala Ala Ala Leu Leu Gln
                 30                  35                  40

GCT CTA GGA CTG CGC GAT GAG CCC CAG GGT GCC CCC AGG CTC CGG CCG       254
Ala Leu Gly Leu Arg Asp Glu Pro Gln Gly Ala Pro Arg Leu Arg Pro
             45                  50                  55

GTT CCC CCG GTC ATG TGG CGC CTG TTT CGA CGC CGG GAC CCC CAG GAG       302
Val Pro Pro Val Met Trp Arg Leu Phe Arg Arg Arg Asp Pro Gln Glu
         60                  65                  70

ACC AGG TCT GGC TCG CGG CGG ACG TCC CCA GGG GTC ACC CTG CAA CCG       350
Thr Arg Ser Gly Ser Arg Arg Thr Ser Pro Gly Val Thr Leu Gln Pro
     75                  80                  85

TGC CAC GTG GAG GAG CTG GGG GTC GCC GGA AAC ATC GTG CGC CAC ATC       398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG       446
Pro Asp Arg Gly Ala Pro Thr Arg Ala Ser Glu Pro Val Ser Ala Ala
                 110                 115                 120

GGG CAT TGC CCT GAG TGG ACA GTC GTC TTC GAC CTG TCG GCT GTG GAA       494
Gly His Cys Pro Glu Trp Thr Val Val Phe Asp Leu Ser Ala Val Glu
             125                 130                 135

CCC GCT GAG CGC CCG AGC CGG GCC CGC CTG GAG CTG CGT TTC GCG GCG       542
Pro Ala Glu Arg Pro Ser Arg Ala Arg Leu Glu Leu Arg Phe Ala Ala
         140                 145                 150

GCG GCG GCA GCC CCG GAG GGC GGC TGG GAG CTG AGC GTG GCG CAA           590
Ala Ala Ala Ala Pro Glu Gly Gly Trp Glu Leu Ser Val Ala Gln
     155                 160                 165

GCG GGC CAG GGC GCG GGC GCG GAC CCC GGG CCG GTG CTG CTC CGC CAG       638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC       686
Leu Val Pro Ala Leu Gly Pro Pro Val Arg Ala Glu Leu Leu Gly Ala
                 190                 195                 200

GCT TGG GCT CGC AAC GCC TCA TGG CCG CGC AGC CTC CGC CTG GCG CTG       734
Ala Trp Ala Arg Asn Ala Ser Trp Pro Arg Ser Leu Arg Leu Ala Leu
             205                 210                 215

GCG CTA CGC CCC CGG GCC CCT GCC GCC TGC GCG CGC CTG GCC GAG GCC       782
Ala Leu Arg Pro Arg Ala Pro Ala Ala Cys Ala Arg Leu Ala Glu Ala
         220                 225                 230

TCG CTG CTG CTG GTG ACC CTC GAC CCG CGC CTG TGC CAC CCC CTG GCC       830
Ser Leu Leu Leu Val Thr Leu Asp Pro Arg Leu Cys His Pro Leu Ala
     235                 240                 245
```

```
CGG CCG CGG CGC GAC GCC GAA CCC GTG TTG GGC GGC GGC CCC GGG GGC      878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG      926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG      974
His Arg Trp Val Ile Ala Pro Arg Gly Phe Leu Ala Asn Tyr Cys Gln
            285                 290                 295

GGT CAG TGC GCG CTG CCC GTC GCG CTG TCG GGG TCC GGG GGG CCG CCG     1022
Gly Gln Cys Ala Leu Pro Val Ala Leu Ser Gly Ser Gly Gly Pro Pro
        300                 305                 310

GCG CTC AAC CAC GCT GTG CTG CGC GCG CTC ATG CAC GCG GCC GCC CCG     1070
Ala Leu Asn His Ala Val Leu Arg Ala Leu Met His Ala Ala Ala Pro
    315                 320                 325

GGA GCC GCC GAC CTG CCC TGC TGC GTG CCC GCG CGC CTG TCG CCC ATC     1118
Gly Ala Ala Asp Leu Pro Cys Cys Val Pro Ala Arg Leu Ser Pro Ile
330                 335                 340                 345

TCC GTG CTC TTC TTT GAC AAC AGC GAC AAC GTG GTG CTG CGG CAG TAT     1166
Ser Val Leu Phe Phe Asp Asn Ser Asp Asn Val Val Leu Arg Gln Tyr
                350                 355                 360

GAG GAC ATG GTG GTG GAC GAG TGC GGC TGC CGC TAACCCGGGG CGGGCAGGGA   1219
Glu Asp Met Val Val Asp Glu Cys Gly Cys Arg
            365                 370

CCCGGGCCCA ACAATAAATG CCGCGTGG                                      1247

(2) INFORMATION FOR SEQ ID NO:33:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:33:

Met Pro Pro Pro Gln Gln Gly Pro Cys Gly His His Leu Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45

Pro Gln Gly Ala Pro Arg Leu Arg Pro Val Pro Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Val Ser Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175
```

-continued

```
Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
            245                 250                 255

Pro Val Leu Gly Gly Gly Pro Gly Gly Ala Cys Arg Ala Arg Arg Leu
            260                 265                 270

Tyr Val Ser Phe Arg Glu Val Gly Trp His Arg Trp Val Ile Ala Pro
            275                 280                 285

Arg Gly Phe Leu Ala Asn Tyr Cys Gln Gly Gln Cys Ala Leu Pro Val
    290                 295                 300

Ala Leu Ser Gly Ser Gly Gly Pro Pro Ala Leu Asn His Ala Val Leu
305                 310                 315                 320

Arg Ala Leu Met His Ala Ala Ala Pro Gly Ala Ala Asp Leu Pro Cys
            325                 330                 335

Cys Val Pro Ala Arg Leu Ser Pro Ile Ser Val Leu Phe Phe Asp Asn
            340                 345                 350

Ser Asp Asn Val Val Leu Arg Gln Tyr Glu Asp Met Val Val Asp Glu
        355                 360                 365

Cys Gly Cys Arg
    370
```

METHOD FOR REDUCING TISSUE DAMAGE ASSOCIATED WITH ISCHEMIA-REPERFUSION OR HYPOXIA INJURY

CROSS REFERENCE RELATIONSHIP TO RELATED APPLICATIONS

This is a continuation of application(s) Ser. No. 08/165,511 filed on Dec. 9, 1993, abandoned, which is a file wrapper continuation of Ser. No. 07/938,336 filed Aug. 28, 1992 (now abandoned), which is a continuation-in-part of (1) U.S. Ser. No. 07/753,059, filed Aug. 30, 1991, now abandoned, which is a continuation-in-part of U.S. Ser. No. 07/667,274, filed Mar. 11, 1991, now abandoned, and (2) U.S. Ser. No. 07/752,764, filed Aug. 30, 1991, now abandoned, which is a continuation-in-part of U.S. Ser. No. 667,274, the disclosure of which are incorporated herein by reference.

FIELD OF THE INVENTION

The present invention relates generally to a method for modulating the inflammatory response induced in a mammal following tissue injury. More particularly, this invention relates to a method for alleviating immune-cell mediated tissue destruction associated with the inflammatory response.

BACKGROUND OF THE INVENTION

The body's inflammatory response to tissue injury can cause significant tissue destruction, leading to loss of tissue function. Damage to cells resulting from the effects of inflammatory response e.g., by immune-cell mediated tissue destruction, has been implicated as the cause of reduced tissue function or loss of tissue function in diseases of the joints (e.g., rheumatoid and osteo-arthritis) and of many organs, including the kidney, pancreas, skin, lung and heart. For example, glomular nephritis, diabetes, inflammatory bowel disease, vascular diseases such as atheroclerosis and vasculitis, and skin diseases such as psoriasis and dermatitis are believed to result in large part from unwanted acute inflammatory reaction and fibrosis. A number of these diseases, including arthritis, psoriasis and inflammatory bowel disease are considered to be chronic inflammatory diseases. The damaged tissue also often is replaced by fibrotic tissue, e.g., scar tissue, which further reduces tissue function. Graft and transplanted organ rejection also is believed to be primarily due to the action of the body's immune/inflammatory response system.

The immune-cell mediated tissue destruction often follows an initial tissue injury or insult. The secondary damage, resulting from the inflammatory response, often is the source of significant tissue damage. Among the factors thought to mediate these damaging effects are those associated with modulating the body's inflammatory response following tissue injury, e.g., cytokines such as interleukin-1 (IL-1) and tumor necrosis factor (TNF), and oxygen-derived free radicals such as superoxide anions. These humoral agents are produced by adhering neutrophilic leukocytes or by endothelial cells and have been identified at ischemic sites upon reperfusion. Moreover, TNF concentrations are increased in humans after myocardial infarction.

A variety of lung diseases are characterized by airway inflammation, including chronic bronchitis, emphysema, idiopathic pulmonary fibrosis and asthma. Another type of lung-related inflammation disorders are inflammatory diseases characterized by a generalized, wide-spread, acute inflammatory response such as adult respiratory distress syndrome. Another dysfunction associated with the inflammatory response is that mounted in response to injury caused by hyperoxia, e.g., prolonged exposure to lethally high concentrations of $O_2$ (95–100% $O_2$). Similarly, reduced blood flow to a tissue (and, therefore reduced or lack of oxygen to tissues), as described below, also can induce a primary tissue injury that stimulates the inflammatory response.

It is well known that damage occurs to cells in mammals which have been deprived of oxygen. In fact, the interruption of blood flow, whether partial (hypoxia) or complete (ischemia) and the ensuing inflammatory responses may be the most important cause of coagulative necrosis or cell death in human disease. The complications of atherosclerosis, for example, are generally the result of ischemic cell injury in the brain, heart, small intestines, kidneys, and lower extremities. Highly differentiated cells, such as the proximal tubular cells of the kidney, cardiac myocytes, and the neurons of the central nervous system, all depend on aerobic respiration to produce ATP, the energy necessary to carry out their specialized functions. When ischemia limits the oxygen supply and ATP is depleted, the affected cells may become irreversibly injured. The ensuing inflammatory responses to this initial injury provide additional insult to the affected tissue. Examples of such hypoxia or ischemia are the partial or total loss of blood supply to the body as a whole, an organ within the body, or a region within an organ, such as occurs in cardiac arrest, pulmonary embolus, renal artery occlusion, coronary occlusion or occlusive stroke.

The tissue damage associated with ischemia-reperfusion injury is believed to comprise both the initial cell damage induced by the deprivation of oxygen to the cell and its subsequent recirculation, as well as the damage caused by the body's response to this initial damage. It is thought that reperfusion injury may result in dysfunction to the endothelium of the vasculature as well as injury to the surrounding tissue. In idiopathic pulmonary fibrosis, for example, scar tissue accumulates on the lung tissue lining, inhibiting the tissue's elasticity. The tissue damage associated with hyperoxia injury is believed to follow a similar mechanism, where the initial damage is mediated primarily through the presence of toxic oxygen metabolites, followed by an inflammatory response to this initial injury.

Similarly, tissues and organs for transplantation also are subject to the tissue destructive effects associated with the recipient host body's inflammatory response following transplantation. It is currently believed that the initial destructive response is due in large part to reperfusion injury to the transplanted organ after it has been transplanted to the organ recipient.

Accordingly, the success of organ or tissue transplantation depends greatly on the preservation of the tissue activity (e.g., tissue or organ viability) at the harvest of the organ, during storage of the harvested organ, and at transplantation. To date, preservation of organs such as lungs, pancreas, heart and liver remains a significant stumbling block to the successful transplantation of these organs. U.S. Pat. No. 4,952,409 describes a superoxide dismutase-containing liposome to inhibit reperfusion injury. U.S. Pat. No. 5,002,965 describes the use of ginkolides, known platelet activating factor antagonists, to inhibit reperfusion injury. Both of these factors are described as working primarily by inhibiting the release of and/or inhibiting the damaging effects of free oxygen radicals. A number of patents also have issued on the use of immunosuppressants for inhibiting graft rejection. A representative listing includes U.S. Pat. Nos. 5,104, 858, 5,008,246 and 5,068,323. A significant problem with many immunosuppressants is their low therapeutic index, requiring the administration of high doses that can have significant toxic side effects.

Rheumatoid and osteoarthritis are prevalent diseases characterized by chronic inflammation of the synovial membrane lining the afflicted joint. A major consequence of chronic inflammatory joint disease (e.g., rheumatoid arthritis) and degenerative arthritis (e.g., osteoarthritis) is loss of function of those affected joints. This loss of function is due primarily to destruction of the major structural components of the joint, cartilage and bone, and subsequent loss of the proper joint anatomy. As a consequence of chronic disease, joint destruction ensues and can lead to irreversible and permanent damage to the joint and loss of function. Current treatment methods for severe cases of rheumatoid arthritis typically include the removal of the synovial membrane, e.g., synovectomy. Surgical synovectomy has many limitations, including the risk of the surgical procedure itself, and the fact that a surgeon often cannot remove all of the diseased membrane. The diseased tissue remaining typically regenerates, causing the same symptoms which the surgery was meant to alleviate.

Psoriasis is a chronic, recurrent, scaling skin disease of unknown etiology characterized by chronic inflammation of the skin. Erythematous eruptions, often in papules or plaques, and usually having a white silvery scale, can affect any part of the skin, but most commonly affect the scalp, elbows, knees and lower back. The disease usually occurs in adults, but children may also be affected. Patients with psoriasis have a much greater incidence of arthritis (psoraitic arthritis), and generalized exfoliation and even death can threaten afflicted individuals.

Current therapeutic regimens include topical or intralesional application of corticosteroids, topical administration of keratolytics, and use of tar and UV light on affected areas. No single therapy is ideal, and it is rare for a patient not to be treated with several alternatives during the relapsing and remitting course of the disease. Whereas systematic treatment can induce prompt resolution of psoriatic lesions, suppression often requires ever-increasing doses, sometimes with toxic side effect, and tapering of therapy may result in rebound phenomena with extensions of lesions, possibly to exfoliation.

Inflammatory bowel disease (IBD) describes a class of clinical disorders of the gastrointestinal mucosa characterized by chronic inflammation and severe ulceration of the mucosa. The two major diseases in this classification are ulcerative colitis and regional enteritis (Crohn's Disease). Like oral mucositis, the diseases classified as IBD are associated with severe mucosal ulceration (frequently penetrating the wall of the bowel and forming strictures and fistulas), severe mucosal and submucosal inflammation and edema, and fibrosis (e.g., scar tissue formation which interferes with the acid protective function of the gastrointestinal lining.) Other forms of IBD include regional ileitis and proctitis. Clinically, patients with fulminant IBD can be severely ill with massive diarrhea, blood loss, dehydration, weight loss and fever. The prognosis of the disease is not good and frequently requires resection of the diseased tissue.

Therefore, an object of the present invention is to provide a method for protecting mammalian tissue, particularly human tissue, from the damage associated with the inflammatory response following a tissue injury. The inflammatory reaction may be in response to an initial tissue injury or insult. The original injury may be chemically, mechanically, immunologically or biologically related. Another object is to provide methods and compositions for protecting tissue from the tissue destructive effects associated with chronic inflammatory diseases, including arthritis (e.g., reheumatoid or osteoarthritis), psoriatic arthritis, psoriasis and dermatitis, inflammatory bowel disease and other autoimmune diseases.

Another object of the invention is to provide methods and compositions for enhancing the viability of mammalian tissues and organs to be transplanted, including protecting the transplanted organs from immune cell-mediated tissue destruction, such as the tissue damage associated with ischemia-reperfusion injury, such as can occur upon initiation of blood flow after transplantation of the organ in the recipient host.

Another object of the invention is to provide a method for alleviating tissue damage associated with ischemic-reperfusion injury in a mammal following a deprivation of oxygen to a tissue in the mammal. Other objects of the present invention include providing a method for alleviating tissue damage associated with ischemic-reperfusion injury in a human which has suffered from hypoxia or ischemia following cardiac arrest, pulmonary embolus, renal artery occlusion, coronary occlusion or occlusive stroke, as well as tissue damage associated with a surgical or other aggressive clinical procedure. Still another object is to provide a method for alleviating tissue damage associated with hyperoxia-induced injury in a human following exposure to lethally high oxygen concentrations.

Still another object of the invention is to provide a method for modulating inflammatory responses in general, particularly those induced in a human following tissue injury.

These and other objects and features of the invention will be apparent from the description, drawings and claims which follow.

SUMMARY OF THE INVENTION

The present invention provides a method for alleviating the tissue destructive effects associated with activation of the inflammatory response following tissue injury. The method comprises the step of providing to the affected tissue a therapeutically effective concentration of a morphogenic protein ("morphogen", as defined herein) upon tissue injury or in anticipation of tissue injury, sufficient to substantially inhibit or reduce the tissue destructive effects of the inflammatory response.

In one aspect, the invention features compositions and therapeutic treatment methods that comprise the step of administering to a mammal a therapeutically effective amount of a morphogenic protein ("morphogen"), as defined herein, upon injury to a tissue, or in anticipation of such injury, for a time and at a concentration sufficient to inhibit the tissue destructive effects associated with the body's inflammatory response, including repairing damaged tissue, and/or inhibiting additional damage thereto.

In another aspect, the invention features compositions and therapeutic treatment methods for protecting tissues and organs from the tissue destructive effects of the inflammatory response which include administering to the mammals upon injury to a tissue or in anticipation of such injury, a compound that stimulates in vivo a therapeutically effective concentration of an endogenous morphogen within the body of the mammal sufficient to protect the tissue from the tissue destructive effects associated with the inflammatory response, including repairing damaged tissue and/or inhibiting additional damage thereto. These compounds are referred to herein as morphogen-stimulating agents, and are understood to include substances which, when administered to a mammal, act on cells of tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

As embodied herein, the term "ischemic-reperfusion injury" refers to the initial damage associated with oxygen deprivation of a cell and the subsequent damage associated with the inflammatory response when the cell is resupplied with oxygen. As embodied herein, the term "hyperoxia-induced injury" refers to the tissue damage associated with prolonged exposure to lethally high doses of oxygen, e.g., greater than 95% $O_2$, including the tissue damage associated with the inflammatory response to the initial toxically high oxygen concentration. Accordingly, as used herein, "toxic oxygen concentrations" refers to the tissue damage associated with the injury induced by both lethally low oxygen concentrations of oxygen (including the complete lack of oxygen), and by lethally high oxygen concentrations. The expression "alleviating" means the protection from, reduction of and/or elimination of undesired tissue destruction, particularly immune cell-mediated tissue destruction. The tissue destruction may be in response to an initial tissue injury, which may be mechanical, chemical or immunological in origin. The expression "enhance the viability of" tissues or organs, as used herein, means protection from, reduction of and/or elimination of reduced or lost tissue or organ function as a result of tissue death, particularly immune cell-mediated tissue death. "Transplanted" living tissue includes both tissue transplants, (e.g., as in the case of bone marrow transplants, for example), and tissue grafts. Finally, a "free oxygen radical inhibiting agent" means a molecule capable of inhibiting the release of and/or inhibiting the tissue damaging effects of free oxygen radicals.

In one embodiment of the invention, the invention provides methods and compositions for alleviating the ischemic-reperfusion injury in mammalian tissue resulting from a deprivation of, and subsequent reperfusion of, oxygen to the tissue. In another embodiment, the invention provides a method for alleviating the tissue-destructive effects associated with hyperoxia. In still another embodiment of the invention, the invention provides methods and compositions for maintaining the viability of tissues and organs, particularly transplanted tissues and organs, including protecting these tissues and organs from ischemia-reperfusion injury. In still another embodiment, the invention provides methods for protecting tissues and organs from the tissue destructive effects of chronic inflammatory diseases, such as arthritis, psoriasis, dermatitis, including contact dermatitis, IBD and other chronic inflammatory diseases of the gastrointestinal tract, as well as the tissue destructive effects associated with other, known autoimmune diseases, such as diabetes, multiple sclerosis, amyotrophic lateral sclerosis (ALS), and other autoimmune neurodegenerative diseases.

In one aspect of the invention, the morphogen is provided to the damaged tissue following an initial injury to the tissue. The morphogen may be provided directly to the tissue, as by injection to the damaged tissue site or by topical administration, or may be provided indirectly, e.g., systemically by oral or parenteral means. Alternatively, as described above, an agent capable of stimulating endogenous morphogen expression and/or secretion may be administered to the mammal. Preferably, the agent can stimulate an endogenous morphogen in cells associated with the damaged tissue. Alternatively, morphogen expression and/or secretion may be stimulated in a distant tissue and the morphogen transported to the damaged tissue by the circulatory system.

In another aspect of the invention, the morphogen is provided to tissue at risk of damage due to immune cell-mediated tissue destruction. Examples of such tissues include tissue grafts and transplanted tissue or organs, as well as any tissue or organ about to undergo a surgical procedure or other clinical procedure likely to either inhibit blood flow to the tissue or otherwise induce an inflammatory response. Here the morphogen or morphogen-stimulating agent preferably is provided to the patient prior to induction of the injury, e.g., as a prophylactic, to provide a cytoprotective effect to the tissue at risk.

The morphogens described herein are envisioned to be useful in enhancing viability of any organ or living tissue to be transplanted The morphogens may be used to particular advantage in lung, heart, kidney, liver and pancreas transplants, as well as in transplantation and/or grafting of skin, gastrointestinal mucosa, bone marrow and other living tissues.

Where the patient suffers from a chronic inflammatory disease, such as diabetes, arthritis, psoriasis, IBD, and the like, the morphogen or morphogen-stimulating agent preferably is administered at regular intervals as a prophylactic, to prevent and/or inhibit the tissue damage normally associated with the disease during flare periods. As above, the morphogen or morphogen-stimulating agent may be provided directly to the tissue at risk, for example by injection or by topical administration, or indirectly, as by systemic e.g., oral or parenteral administration.

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) *PNAS* 88:4250–4254), all of which are presented in Table II and Seq. ID Nos. 5–14), and the recently identified 60A protein (from Drosophila, Seq. ID No. 24, see Wharton et al. (1991) *PNAS* 88:9214–9218.) The members of this family, which include members of the TGF-β superfamily of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic and species variants thereof, e.g., human OP-1 ("hOP-1", Seq. ID No. 5, mature |

TABLE I-continued

| | |
|---|---|
| | protein amino acid sequence), or mouse OP-1 ("mOP-1", Seq. ID No, 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1) and 292–430 (mOP1). The "pro" regions of the proteins, cleaved to yield the mature, morphogenically active proteins are defined essentially by residues 30–292 (hOP1) and residues 30–291 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2) and 261–399 (mOP2). The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for both OP-2 proteins.) |
| "CBMP2" | refers generically to the morphogenically active proteins expressed from a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) Science 242:1528–1534. The pro domain for BMP2 (BMP2A) likely includes residues 25–248 or 25–282; the mature protein, residues 249–396 or 283–396. The pro domain for BMP4 (BMP2B) likely includes residues 25–256 or 25–292; the mature protein, residues 257–408 or 293–408. |
| "DPP(fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81–84. The pro domain likely extends from the signal peptide cleavage site to residue 456; the mature protein likely is defined by residues 457–588. |
| "Vgl(fx)" | refers to protein sequences encoded by the Xenopus Vgl gene and defining the conserved seven cysteine skeleton (Seq. ID No. 12). The amino acid sequence for the full length protein appears in Weeks (1987) Cell 51: 861–867. The prodomain likely extends from the signal peptide cleavage site to residue 246; the mature protein likely is defined by residues 247–360. |
| "Vgr-1(fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554–4558. The prodomain likely extends from the signal peptide cleavage site to residue 299; the mature protein likely is defined by residues 300–438. |
| "GDF-1(fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The prodomain likely extends from the signal peptide clavage site to residue 214; the mature protein likely is defined by residues 215–372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The prodomain likely extends from the signal peptide cleavage site to residue 324; the mature protein likely is defined by residues 325–455. |
| "BMP3(fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528–1534. The pro domain likely extends from the signal peptide cleavage site to residue 290; the mature protein likely is defined by residues 291–472. |
| "BMP5(fx)" | refers to protein sequences encoded by the human BMP5 gene and defining the conserved seven cysteine skeleton (Seq. ID No. 27). The amino acid sequence for the full length protein appears in Celeste, et al. (1991) PNAS 87: 9843–9847. The pro domain likely extends from the signal peptide cleavage site to residue 316; the mature protein likely is defined by residues 317–454. |
| "BMP6(fx)" | refers to protein sequences encoded by the human BMP6 gene and defining the conserved seven cysteine skeleton (Seq. ID No. 28). The amino acid sequence for the full length protein appears in Celeste, et al. (1990) PNAS 87: 9843–5847. The pro domain likely includes extends from the signal peptide cleavage site to residue 374; the mature sequence likely includes residues 375–513. |

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention (e.g., asheterodimers). Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

```
Cys Xaa Xaa Xaa Xaa        (Seq. ID No. 15)
 1           5
```

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

```
                    Generic Sequence 3
        Leu Tyr Val Xaa Phe
         1           5

Xaa Xaa Xaa Gly Trp Xaa Xaa Trp Xaa
                    10

Xaa Ala Pro Xaa Gly Xaa Xaa Ala
     15              20

Xaa Tyr Cys Xaa Gly Xaa Cys Xaa
            25                  30

Xaa Pro Xaa Xaa Xaa Xaa Xaa
                    35

Xaa Xaa Xaa Asn His Ala Xaa Xaa
            40                  45

Xaa Xaa Leu Xaa Xaa Xaa Xaa Xaa
                    50

Xaa Xaa Xaa Xaa Xaa Xaa Xaa Cys
     55                      60

Cys Xaa Pro Xaa Xaa Xaa Xaa
                    65

Xaa Xaa Xaa Leu Xaa Xaa Xaa
     70                  75

Xaa Xaa Xaa Xaa Val Xaa Leu Xaa
                    80

Xaa Xaa Xaa Xaa Met Xaa Val Xaa
     85                  90

Xaa Cys Gly Cys Xaa
              95
``` wherein each Xaa is independently selected from a group of one or more specified amino acids defined as follows: "Res." means "residue" and Xaa at res.4=(Ser. Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

```
                     Generic Sequence 4
        Cys Xaa Xaa Xaa Xaa Leu Tyr Val Xaa Phe
         1               5                   10

Xaa Xaa Xaa Gly Trp Xaa Xaa Trp Xaa
                        15

Xaa Ala Pro Xaa Gly Xaa Xaa Ala
         20                  25

Xaa Tyr Cys Xaa Gly Xaa Cys Xaa
                30                  35

Xaa Pro Xaa Xaa Xaa Xaa Xaa
                        40

Xaa Xaa Xaa Asn His Ala Xaa Xaa
                    45                  50

Xaa Xaa Leu Xaa Xaa Xaa Xaa Xaa
                        55

Xaa Xaa Xaa Xaa Xaa Xaa Xaa Cys
         60                          65

Cys Xaa Pro Xaa Xaa Xaa Xaa Xaa
                        70

Xaa Xaa Xaa Leu Xaa Xaa Xaa
         75                  80

Xaa Xaa Xaa Xaa Val Xaa Leu Xaa
                        85

Xaa Xaa Xaa Xaa Met Xaa Val Xaa
         90                  95

Xaa Cys Gly Cys Xaa
                    100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24–25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

```
                     Generic Sequence 5
        Leu Xaa Xaa Xaa Phe
         1               5

Xaa Xaa Xaa Gly Trp Xaa Xaa Trp Xaa
                        10

Xaa Xaa Pro Xaa Xaa Xaa Xaa Ala
         15                  20

Xaa Tyr Cys Xaa Gly Xaa Cys Xaa
                    25                  30

Xaa Pro Xaa Xaa Xaa Xaa Xaa
                        35

Xaa Xaa Xaa Asn His Ala Xaa Xaa
                    40                  45

Xaa Xaa Xaa Xaa Xaa Xaa Xaa
```

Generic Sequence 5

```
                    50
    Xaa Xaa Xaa Xaa Xaa Xaa Xaa Cys
        55                      60

Cys Xaa Pro Xaa Xaa Xaa Xaa Xaa
                    65

Xaa Xaa Xaa Leu Xaa Xaa Xaa
        70                  75

Xaa Xaa Xaa Xaa Val Xaa Leu Xaa
                    80

Xaa Xaa Xaa Xaa Met Xaa Val Xaa
        85                      90

Xaa Cys Xaa Cys Xaa
            95
``` wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8 =(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18 =(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

```
    Cys Xaa Xaa Xaa Xaa Leu Xaa Xaa Xaa Phe
    1                   5                   10

Xaa Xaa Xaa Gly Trp Xaa Xaa Trp Xaa
                    15

Xaa Xaa Pro Xaa Xaa Xaa Xaa Ala
        20                  25

Xaa Tyr Cys Xaa Gly Xaa Cys Xaa
                30                  35

Xaa Pro Xaa Xaa Xaa Xaa Xaa
                    40

Xaa Xaa Xaa Asn His Ala Xaa Xaa
                45                  50

Xaa Xaa Xaa Xaa Xaa Xaa Xaa Xaa
                    55

Xaa Xaa Xaa Xaa Xaa Xaa Xaa Cys
        60                      65

Cys Xaa Pro Xaa Xaa Xaa Xaa Xaa
                    70

Xaa Xaa Xaa Leu Xaa Xaa Xaa
        75                  80

Xaa Xaa Xaa Xaa Val Xaa Leu Xaa
                    85

Xaa Xaa Xaa Xaa Met Xaa Val Xaa
            90                  95

Xaa Cys Xaa Cys Xaa
            100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58=(Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His);

Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-l, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J. Mol. Biol.* 48:443–453) and identities calculated by the Align program (DNAstar, Inc.). "Homology" or "similarity" as used herein includes allowed conservative changes as defined by Dayoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 29).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens useful in the methods, compositions and devices of this invention is disclosed in copending U.S. patent application Ser. Nos. 752,764, filed Aug. 30, 1991, and 667,274, filed Mar. 11, 1991, the disclosure of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of protecting tissues and organs from immune cell-mediated tissue destruction, including substantially inhibiting such damage and/or regenerating the damaged tissue in a variety of mammals, including humans.

The foregoing and other objects, features and advantages of the present invention will be made more apparent from the following detailed description of the invention.

DETAILED DESCRIPTION OF THE INVENTION

Figure 1:
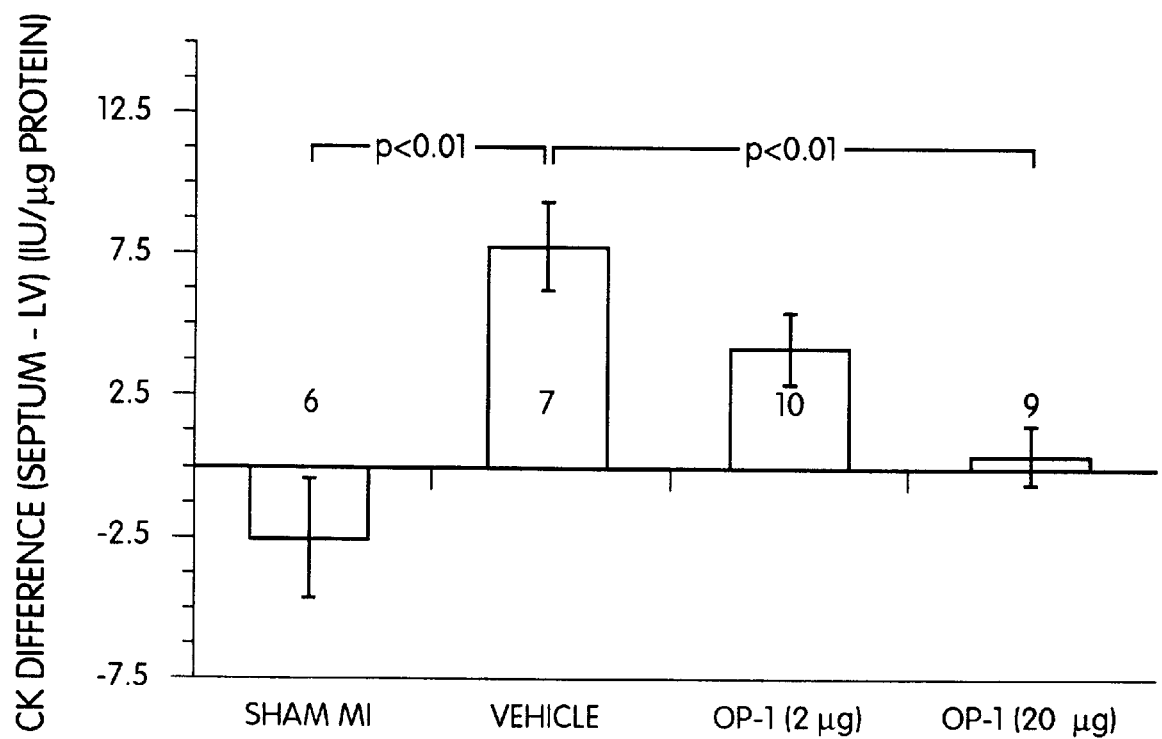
FIG. 1 shows the cardioprotective effects of morphogen (hOP1) in a rat myocardial ischemia-reperfusion model, as evidenced by the smaller loss of myocardial creatine kinase in hOP1-treated rats.

It now has been surprisingly discovered that the morphogens defined herein are effective agents in alleviating the tissue destructive effects associated with the body's inflammatory response to tissue injury. In particular, as disclosed herein, the morphogens are capable of alleviating the necrotic tissue effects associated with the ensuing inflammatory responses that occur following an initial tissue injury.

When tissue injury occurs, whether caused by bacteria, trauma, chemicals, heat, or any other phenomenon, the body's inflammatory response is stimulated. In response to signals released from the damaged cells (e.g., cytokines), extravascularization of immune effector cells is induced. Under ordinary circumstances these invading immune effector cells kill the infectious agent and/or infected or damaged cells (through the release of killing substances such as superoxides, performs, and other antimicrobial agents stored in granules), remove the dead tissues and organisms (through phagocytosis), release various biological response modifiers that promote rapid healing and covering of the wound (quite often resulting in the formation of fibrotic scar tissue), and then, after the area is successfully healed, exit from the site of the initial insult. Once the site is perceived to be normal, the local release of inflammatory cytokines ceases and the display of adhesion molecules on the vessel endothelium returns to basal levels. In some cases, however, the zeal of these interacting signals and cellular systems, which are designed to capture and contain very rapidly multiplying infectious agents, act to the detriment of the body, killing additional, otherwise healthy, surrounding tissue. This additional unnecessary tissue death further compromises organ function and sometimes results in death of the individual. In addition, the resulting scar tissue that often forms can interfere with normal tissue function as occurs, for example, in idiopathic pulmonary fibrosis, IBD and organ cirrhosis.

The vascular endothelium constitutes the first barrier between circulating immune effector cells and extravascular tissues. Extravasation of these circulating cells requires that they bind to the vascular endothelial cells, cross the basement membrane, and enter insulted tissues e.g., by phagocytosis or protease-mediated extracellular matrix degradation. Without being limited to a particular theory, it is believed that the morphogens of this invention may modulate the inflammatory response in part by modulating the attachment of immune effector cells to the luminal side of the endothelium of blood vessels at or near sites of tissue damage and/or inflammatory lesions. Because the method reduces or prevents the attachment of immune effector cells at these sites, it also prevents the subsequent release of tissue destructive agents by these same immune effector cells at sites of tissue damage and/or inflammatory lesions. Because attachment of immune effector cells to the endothelium must precede their extravascularization, the method also prevents the initial or continued entry of these cells into extravascular sites of tissue destruction or ongoing inflammatory lesions. Therefore, the invention not only relates to a method to reduce or prevent the immune cell-mediated cellular destruction at extravascular sites of recent tissue destruction, but also relates to a method to prevent or reduce the continued entry of immune effector cells into extravascular sites of ongoing inflammatory cascades. As will be appreciated by those skilled in the art, the morphogens of this invention also may be contemplated in mechanisms for disrupting the functional interaction of immune effector cells with endothelium where the adhesion molecules are induced by means other than in response to tissue injury.

One source of tissue damage follows cell exposure to toxic oxygen concentrations, such as the tissue damage following ischemic-reperfusion tissue injury (oxygen deprivation), and following hyperoxia injury (lethally high oxygen concentrations). Accordingly, the process of the present invention provides a method for alleviating the tissue damage induced by ischemic-reperfusion injury or hyperoxia-induced injury comprising the step of administering to the afflicted individual a therapeutic amount of a morphogen prior to, during, or after damage to the affected tissue. Where the toxic oxygen concentrations may be deliberately or unavoidably induced, as by a surgical or clinical procedure, the morphogen preferably is administered prior to induction.

In addition, the morphogens described herein, in contrast to fibrogenic growth factors such as TGF-β, stimulate tissue morphogenesis and do not stimulate fibrosis or scar tissue formation (see Example 9, below.) Accordingly, in addition to inhibiting the tissue destructive effects associated with the inflammatory response, the morphogens further enhance the viability of damaged tissue and/or organs by stimulating the regeneration of the damaged tissue and preventing fibrogenesis.

The morphogens described herein also can inhibit epithelial cell proliferation (see Example 10, below.) This activity of the morphogens also may be particularly useful in the treatment of psoriasis and other inflammatory diseases that involve epithelial cell populations.

Provided below are detailed descriptions of suitable morphogens useful in the methods and compositions of this invention, as well as methods for their administration and application, and numerous, nonlimiting examples which 1) illustrate the suitability of the morphogens and morphogen-stimulating agents described herein as therapeutic agents for protecting tissue from the tissue destructive effects associated with the body's inflammatory response; and 2) provide assays with which to test candidate morphogens and morphogen-stimulating agents for their efficacy.

I. USEFUL MORPHOGENS

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, the disclosures of which are hereinabove incorporated by reference.

A candidate morphogen or morphogen composition can be evaluated for in vivo morphogenic utility generally according to the procedures set forth in U.S. Ser. No. 07/752,764. The proteins and compositions may be injected or surgically implanted in a mammal, following any of a number of procedures well known in the art. For example, surgical implant bioassays may be performed essentially following the procedure of Sampath et al. (1983) *PNAS* 80:6591–6595.

Histological sectioning and staining is preferred to determine the extent of morphogenesis in vivo, particularly in tissue repair procedures. Excised implants are fixed in Bouins Solution, embedded in paraffin, and cut into 6–8 µm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;
(2) mesenchymal cell migration and proliferation on days two and three;
(3) chondrocyte appearance on days five and six;
(4) cartilage matrix formation on day seven;
(5) cartilage calcification on day eight;
(6) vascular invasion, appearance of osteoblasts, and formation of new bone on days nine and ten;
(7) appearance of osteoblastic and bone remodeling and dissolution of the implanted matrix on days twelve to eighteen; and
(8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labeled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity. Alternatively, novel morphogenic sequences may be identified following the procedures disclosed therein.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6). Generic sequences 1 and 2 also may include, at their N-terminus, the sequence

```
Cys Xaa Xaa Xaa Xaa        (Seq. ID No. 15)
 1               5
```

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | |
|---|---|---|---|---|---|---|---|
| hOP-1 | Cys | Lys | Lys | His | Glu | Leu | Tyr | Val |
| mOP-1 | — | — | — | — | — | — | — | — |
| hOP-2 | — | Arg | Arg | — | — | — | — | — |
| mOP-2 | — | Arg | Arg | — | — | — | — | — |
| DPP | — | Arg | Arg | — | Ser | — | — | — |
| Vgl | — | — | Lys | Arg | His | — | — | — |
| Vgr-1 | — | — | — | — | Gly | — | — | — |
| CBMP-2A | — | — | Arg | — | Pro | — | — | — |
| CBMP-2B | — | Arg | Arg | — | Ser | — | — | — |
| BMP3 | — | Ala | Arg | Arg | Tyr | — | Lys | — |
| GDF-1 | — | Arg | Ala | Arg | Arg | — | — | — |
| 60A | — | Gln | Met | Glu | Thr | — | — | — |
| BNP5 | — | — | — | — | — | — | — | — |
| BMP6 | — | Arg | — | — | — | — | — | — |

TABLE II-continued

| | | | | | | | | |
|---|---|---|---|---|---|---|---|---|
| hOP-1 | Ser | Phe | Arg | Asp | Leu | Gly | Trp | Gln | Asp |
| mOP-1 | — | — | — | — | — | — | — | — | — |
| hOP-2 | — | — | Gln | — | — | — | — | Leu | — |
| mOP-2 | Ser | — | — | — | — | — | — | Leu | — |
| DPP | Asp | — | Ser | — | Val | — | — | Asp | — |
| Vgl | Glu | — | Lys | — | Val | — | — | — | Asn |
| Vgr-1 | — | — | Gln | — | Val | — | — | — | — |
| CBMP-2A | Asp | — | Ser | — | Val | — | — | Asn | — |
| CBMP-2B | Asp | — | Ser | — | Val | — | — | Asn | — |
| BMP3 | Asp | — | Ala | — | Ile | — | — | Ser | Glu |
| GDF-1 | — | — | — | Glu | Val | — | — | His | Arg |
| 60A | Asp | — | Lys | — | — | — | — | His | — |
| BMP5 | — | — | — | — | — | — | — | — | — |
| BMP6 | — | — | Gln | — | — | — | — | — | — |
| hOP-1 | Trp | Ile | Ile | Ala | Pro | Glu | Gly | Tyr | Ala |
| mOP-1 | — | — | Gln | — | — | — | — | — | — |
| hOP-2 | — | Val | — | — | — | Gln | — | — | Ser |
| mOP-2 | — | Val | — | — | — | Gln | — | — | Ser |
| DPP | — | — | Val | — | — | Leu | — | — | Asp |
| Vgl | — | Val | — | — | — | Gln | — | — | Met |
| Vgr-1 | — | — | — | — | — | Lys | — | — | — |
| CBMP-2A | — | — | Val | — | — | Pro | — | — | His |
| CBMP-2B | — | — | Val | — | — | Pro | — | — | Gln |
| BMP3 | — | — | — | Ser | — | Lys | Ser | Phe | Asp |
| GDF-1 | — | Val | — | — | — | Arg | — | Phe | Leu |
| 60A | — | — | — | — | — | — | — | — | Gly |
| BMP5 | — | — | — | — | — | — | — | — | — |
| BMP6 | — | — | — | — | — | Lys | — | — | — |
| hOP-1 | Ala | Tyr | Tyr | Cys | Glu | Gly | Glu | Cys | Ala |
| mOP-1 | — | — | — | — | — | — | — | — | — |
| hOP-2 | — | — | — | — | — | — | — | — | Ser |
| mOP-2 | — | — | — | — | — | — | — | — | — |
| DPP | — | — | — | — | His | — | Lys | — | Pro |
| Vgl | — | Asn | — | — | Tyr | — | — | — | Pro |
| Vgr-1 | — | Asn | — | — | Asp | — | — | — | Ser |
| CBMP-2A | — | Phe | — | — | His | — | Glu | — | Pro |
| CBMP-2B | — | Phe | — | — | His | — | Asp | — | Pro |
| BMP3 | — | — | — | — | Ser | — | Ala | — | Gln |
| GDF-1 | — | Asn | — | — | Gln | — | Gln | — | — |
| 60A | — | Phe | — | — | Ser | 13 | — | — | Asn |
| BMP5 | — | Phe | — | — | Asp | — | — | — | Ser |
| BMP6 | — | Asn | — | — | Asp | — | — | — | Ser |
| hOP-1 | Phe | Pro | Leu | Asn | Ser | Tyr | Met | Asn | Ala |
| mOP-1 | — | — | — | — | — | — | — | — | — |
| hOP-2 | — | — | — | Asp | — | Cys | — | — | — |
| mOP-2 | — | — | — | Asp | — | Cys | — | — | — |
| DPP | — | — | — | Ala | Asp | His | Phe | — | Ser |
| Vgl | Tyr | — | — | Thr | Glu | Ile | Leu | — | Gly |
| Vgr-1 | — | — | — | — | Ala | His | — | — | — |
| CBMP-2A | — | — | — | Ala | Asp | His | Leu | — | Ser |
| CBMP-2B | — | — | — | Ala | Asp | His | Leu | — | Ser |
| GDF-1 | Leu | — | Val | Ala | Leu | Ser | Gly | Ser** | — |
| BMP3 | — | — | Met | Pro | Lys | Ser | Leu | Lys | Pro |
| 60A | — | — | — | — | Ala | His | — | — | — |
| BMP5 | — | — | — | — | Ala | His | Met | — | — |
| BMP6 | — | — | — | — | Ala | His | Met | — | — |
| hOP-1 | Thr | Asn | His | Ala | Ile | Val | Gln | Thr | Leu |
| mOP-1 | — | — | — | — | — | — | — | — | — |
| hOP-2 | — | — | — | — | — | Leu | — | Ser | — |
| mOP-2 | — | — | — | — | — | Leu | — | Ser | — |
| DPP | — | — | — | — | Val | — | — | — | — |
| Vgl | Ser | — | — | — | — | Leu | — | — | — |
| Vgr-1 | — | — | — | — | — | — | — | — | — |
| CBMP-2A | — | — | — | — | — | — | — | — | — |
| CBMP-2B | — | — | — | — | — | — | — | — | — |
| BMP3 | Ser | — | — | — | Thr | Ile | — | Ser | Ile |
| GDF-1 | Leu | — | — | — | Val | Leu | Arg | Ala | — |
| 60A | — | — | — | — | — | — | — | — | — |
| BMP5 | — | — | — | — | — | — | — | — | — |
| BMP6 | — | — | — | — | — | — | — | — | — |
| hOP-1 | Val | His | Phe | Ile | Asn | Pro | Glu | Thr | Val |
| mOP-1 | — | — | — | — | — | Asp | — | — | — |
| hOP-2 | — | His | Leu | Met | Lys | — | Asn | Ala | — |
| mOP-2 | — | His | Leu | Met | Lys | — | Asp | Val | — |
| DPP | — | Asn | Asn | Asn | — | — | Gly | Lys | — |
| Vgl | — | — | Ser | — | Glu | — | — | Asp | Ile |
| Vgr-1 | — | — | Val | Met | — | — | — | Tyr | — |
| CBMP-2A | — | Asn | Ser | Val | — | Ser | — | Lys | Ile |
| CBMP-2B | — | Asn | Ser | Val | — | Ser | — | Ser | Ile |

TABLE II-continued

| | | | | | | | | | |
|---|---|---|---|---|---|---|---|---|---|
| BMP3 | — | Arg | Ala** | Gly | Val | Val | Pro | Gly | Ile |
| GDF-1 | Met | — | Ala | Ala | Ala | — | Gly | Ala | Ala |
| 60A | — | — | Leu | Leu | Glu | — | Lys | Lys | — |
| BMP5 | — | — | Leu | Met | Phe | — | Asp | His | — |
| BMP6 | — | — | Leu | Met | — | — | — | Tyr | — |
| hOP-1 | Pro | Lys | Pro | Cys | Cys | Ala | Pro | Thr | Gln |
| mOP-1 | — | — | — | — | — | — | — | — | — |
| hOP-2 | — | — | Ala | — | — | — | — | — | Lys |
| mOP-2 | — | — | Ala | — | — | — | — | — | Lys |
| DPP | — | — | Ala | — | — | Val | — | — | — |
| Vgl | — | Leu | — | — | — | Val | — | — | Lys |
| Vgr-1 | — | — | — | — | — | — | — | — | Lys |
| CBMP-2A | — | — | Ala | — | — | Val | — | — | Glu |
| CBMP-2B | — | — | Ala | — | — | Val | — | — | Glu |
| BMP3 | — | Glu | — | — | — | Val | — | Glu | Lys |
| GDF-1 | Asp | Leu | — | — | — | Val | — | Ala | Arg |
| 60A | — | — | — | — | — | — | — | — | Arg |
| BMP5 | — | — | — | — | — | — | — | — | Lys |
| BMP6 | — | — | — | — | — | — | — | — | Lys |
| hOP-1 | Leu | Asn | Ala | Ile | Ser | Val | Leu | Tyr | Phe |
| mOP-1 | — | — | — | — | — | — | — | — | — |
| hOP-2 | — | Ser | — | Thr | — | — | — | — | Tyr |
| mOP-2 | — | Ser | — | Thr | — | — | — | — | Tyr |
| Vgl | Met | Ser | Pro | — | — | Met | — | Phe | Tyr |
| Vgr-1 | Val | — | — | — | — | — | — | — | — |
| DPP | — | Asp | Ser | Val | Ala | Met | — | — | Leu |
| CBMP-2A | — | Ser | — | — | — | Met | — | — | Leu |
| CBMP-2B | — | Ser | — | — | — | Met | — | — | Leu |
| BMP3 | Met | Ser | Ser | Leu | — | Ile | — | Phe | Tyr |
| GDF-1 | — | Ser | Pro | — | — | — | — | Phe | — |
| 60A | — | Gly | — | Leu | Pro | — | — | — | His |
| BMP5 | — | — | — | — | — | — | — | — | — |
| BMP6 | — | — | — | — | — | — | — | — | — |
| hOP-1 | Asp | Asp | Ser | Ser | Asn | Val | Ile | Leu | Lys |
| mOP-1 | — | — | — | — | — | — | — | — | — |
| hOP-2 | — | Ser | — | Asn | — | — | — | — | Arg |
| mOP-2 | — | Ser | — | Asn | — | — | — | — | Arg |
| DPP | Asn | — | Gln | — | Thr | — | Val | — | — |
| Vgl | — | Asn | Asn | Asp | — | — | Val | — | Arg |
| Vgr-1 | — | — | Asn | — | — | — | — | — | — |
| CBMP-2A | — | Glu | Asn | Glu | Lys | — | Val | — | — |
| CBMP-2B | — | Glu | Tyr | Asp | Lys | — | Val | — | — |
| BMP3 | — | Glu | Asn | Lys | — | — | Val | — | — |
| GDF-1 | — | Asn | — | Asp | — | — | Val | — | Arg |
| 60A | Leu | Asn | Asp | Glu | — | — | Asn | — | — |
| BMP5 | — | — | — | — | — | — | — | — | — |
| BMP6 | — | — | Asn | — | — | — | — | — | — |
| hOP-1 | Lys | Tyr | Arg | Asn | Met | Val | Val | Arg | |
| mOP-1 | — | — | — | — | — | — | — | — | |
| hOP-2 | — | His | — | — | — | — | — | Lys | |
| mOP-2 | — | His | — | — | — | — | — | Lys | |
| DPP | Asn | — | Gln | Glu | — | Thr | — | Val | |
| Vgl | His | — | Glu | — | — | Ala | — | Asp | |
| Vgr-1 | — | — | — | — | — | — | — | — | |
| CBMP-2A | Asn | — | Gln | Asp | — | — | — | Glu | |
| CBMP-2B | Asn | — | Gln | Glu | — | — | — | Glu | |
| BMP3 | Val | — | Pro | — | — | Thr | — | Glu | |
| GDF-1 | Gln | — | Glu | Asp | — | — | — | Asp | |
| 60A | — | — | — | — | — | Ile | — | Lys | |
| BMP5 | — | — | — | — | — | — | — | — | |
| BMP6 | — | — | — | Trp | — | — | — | — | |
| hOP-1 | Ala | Cys | Gly | Cys | His | | | | |
| mOP-1 | — | — | — | — | — | | | | |
| hOP-2 | — | — | — | — | — | | | | |
| mOP-2 | — | — | — | — | — | | | | |
| DPP | Gly | — | — | — | Arg | | | | |
| Vgl | Glu | — | — | — | Arg | | | | |
| Vgr-1 | — | — | — | — | — | | | | |
| CBMP-2A | Gly | — | — | — | Arg | | | | |
| CBMP-2B | Gly | — | — | — | Arg | | | | |
| BMP3 | Ser | — | Ala | — | Arg | | | | |
| GDF-1 | Glu | — | — | — | Arg | | | | |
| 60A | Ser | — | — | — | — | | | | |
| BMP5 | Ser | — | — | — | — | | | | |
| BMP6 | — | — | — | — | — | | | | |

**Between residues 56 and 57 of BMP3 is a Val residue; between residues 43 and 44 of GDF-1 lies the amino acid sequence Gly-Gly-Pro-Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. FORMULATIONS AND METHODS FOR ADMINISTERING THERAPEUTIC AGENTS

The morphogens may be provided to an individual by any suitable means, preferably directly (e.g., locally, as by injection or topical administration to a tissue locus) or systemically (e.g., parenterally or orally). Where the morphogen is to be provided parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (9.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, association of the mature dimer with the pro domain of the morphogen keeps the morphogen soluble in physiological buffers. In fact, the endogenous protein is thought to be transported in this form. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the morphogen at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the morphogen in vivo. Other potentially useful parenteral delivery systems for these morphogens include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration.

Suppositories for rectal administration also may be prepared by mixing the morphogen or morphogen-stimulating agent with a non-irritating excipient such as cocoa butter or other compositions which are solid at room temperature and liquid at body temperatures.

Formulations for topical administration to the skin surface may be prepared by dispersing the morphogen or morphogen-stimulating agent with a dermatologically acceptable carrier such as a lotion, cream, ointment or soap. Particularly useful are carriers capable of forming a film or layer over the skin to localize application and inhibit removal. For topical administration to internal tissue surfaces, the morphogen may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

Alternatively, the morphogens described herein may be administered orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590.) In addition, at least one morphogen, OP-1, has been identified in mammary gland extract, colostrum and 57-day milk. Moreover, the OP-1 purified from mammary gland extract is morphogenically active. Specifically, this protein induces endochondral bone formation in mammals when implanted subcutaneously in association with a suitable matrix material, using a standard in vivo bone assay, such as is disclosed in U.S. Pat. No. 4,968,590. Moreover, the morphogen also is detected in the bloodstream. Finally, soluble form morphogen, e.g., mature morphogen associated with the pro domain, is morphogenically active. These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also may be associated with molecules capable of enhancing their solubility in vitro or in vivo.

The compounds provided herein also may be associated with molecules capable of targeting the morphogen or morphogen-stimulating agent to the desired tissue. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences typically diverge significantly in the sequences which define the pro domain. Accordingly, the pro domain is thought to be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of the pro domains which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting morphogen to a tissue of interest is part or all of a morphogen pro domain. For example, part or all of the pro domain of GDF-1, may be used to target a morphogen to nerve tissue. Alternatively, part or all of the pro domains of OP-1 or CBMP2 may be used to target a morphogen to bone tissue, both of which proteins are found naturally associated with bone tissue.

The morphogens described herein are useful for providing neuroprotective effects to alleviate neural pathway damage associated with the body's immune/inflammatory response to an initial injury to nerve tissue. As used herein, a "neural pathway" describes a nerve circuit for the passage of electric signals from a source to a target cell site and includes both the central nervous system (CNS) and peripheral nervous system (PNS). The pathway includes the neurons through which the electric impulse is transported, including groups of interconnecting neurons, the nerve fibers formed by bundled neuronal axons, and the glial cells surrounding and associated with the neurons. An inflammatory response to nerve tissue injury may follow trauma to nerve tissue, caused, for example, by an autoimmune (including autoantibody) dysfunction, neoplastic lesion, infection, chemical or mechanical trauma, or other disease. An exemplary nerve-related inflammatory disease is multiple sclerosis. Neural pathway damage also can result from a reduction or interruption, e.g., occlusion, of a neural blood supply, as in an embolic stroke, (e.g, ischemia or hypoxia-induced injury), or by other trauma to the nerve or surrounding material. In addition, at least part of the damage associated with a number of primary brain tumors also appears to be immunologically related. Application of the morphogen directly to the cells to be treated, or providing the morphogen to the mammal systemically, for example, intravenously or indirectly by oral administration, may be used to alleviate and/or inhibit the immunologically related response to a neural injury. Alternatively, administration of an agent capable of stimulating morphogen expression and/or secretion in vivo, preferably at the site of injury, also may be used. Where the injury is to be induced, as during surgery or other aggressive clinical treatment, the morphogen or agent may be provided prior to induction of the injury to provide a neuroprotective effect to the nerve tissue at risk.

Where the morphogen is intended for use as a therapeutic to alleviate tissue damage associated with an immune/inflammatory condition of the central nervous system (CNS) an additional problem must be addressed: overcoming the so-called "blood-brain barrier", the brain capillary wall structure that effectively screens out all but selected categories of molecules present in the blood, preventing their passage into the brain. The blood-brain barrier may be bypassed effectively by direct infusion of the morphogen or morphogen-stimulating agent into the brain. Alternatively, the morphogen or morphogen-stimulating agent may be modified to enhance its transport across the blood-brain barrier. For example, truncated forms of the morphogen or a morphogen-stimulating agent may be most successful. Alternatively, the morphogen or morphogen-stimulating agent may be modified to render it more lipophilic, or it may be conjugated to another molecule which is naturally transported across the barrier, using standard means known to those skilled in the art, as, for example, described in Pardridge, *Endocrine Reviews:* 7:314–330 (1986) and U.S. Pat. No. 4,801,575. A more detailed description of morphogens for use in treating inflammatory conditions in nerve tissue, including a model for evaluating morphogen transport across the blood brain barrier is disclosed in U.S. Ser. No. 922,813, the disclosure of which is incorporated herein by reference.

Finally, the morphogens or morphogen-stimulating agents provided herein may be administered alone or in combination with other molecules known to be beneficial in the treatment compositions and methods described herein, including, but not limited to anticoagulants, free oxygen radical inhibiting agents, salicylic acid, vitamin D, and other antiinflammatory agents. Psoriais treatments also may include ultra-violet light treatment, zinc oxide and retinoids.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated for parenteral or oral administration to humans or other mammals in therapeutically effective amounts, e.g., amounts which provide appropriate concentrations for a time sufficient to alleviate the tissue destructive effects associated with the inflammatory response, including protecting tissue in anticipation of tissue damage.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of progression of the tissue damage, the overall health status of the particular patient, the relative biological efficacy of the compound selected, the formulation of the compound excipients, and its route of administration. In general terms, the compounds of this invention may be provided in an aqueous physiological buffer solution containing about 0.001% to 10% w/v compound for parenteral administration. Typical dose ranges are from about 10 ng/kg to about 1 g/kg of body weight per day; a preferred dose range is from about 0.1 µg/kg to 100 mg/kg of body weight per day. Optimally, the morphogen dosage given in most cases is between 0.1–100 µg of protein per kilogram weight of the patient. No obvious morphogen induced pathological lesions are induced when mature morphogen (e.g., OP-i, 20 µg) is administered daily to normal growing rats for 21 consecutive days. Moreover, 10 µg systemic injections of morphogen (e.g., OP-1) injected daily for 10 days into normal newborn mice does not produce any gross abnormalities.

In administering morphogens systemically in the methods of the present invention, preferably a large volume loading dose is used at the start of the treatment. The treatment then is continued with a maintenance dose. Further administration then can be determined by monitoring at intervals the levels of the morphogen in the blood.

Where tissue injury is induced deliberately as part of, for example, a surgical procedure, the morphogen preferably is provided just prior to, or concomitant with induction of the trauma. Preferably, the morphogen is administered prophylactically in a surgical setting.

Alternatively, an effective amount of an agent capable of stimulating endogenous morphogen levels may be administered by any of the routes described above. For example, an agent capable of stimulating morphogen production and/or secretion from cells of affected tissue or a transplanted organ may be provided to a mammal, e.g., by direct administration of the morphogen to the tissue or organ. A method for identifying and testing agents capable of modulating the levels of endogenous morphogens in a given tissue is described generally herein in Example 15, and in detail in copending U.S. Ser. No. 752,859, filed Aug. 30, 1991, the disclosure of which is incorporated herein by reference. Briefly, candidate compounds can be identified and tested by incubating the compound in vitro with a test tissue or cells thereof, for a time sufficient to allow the compound to affect the production, i.e., the expression and/or secretion, of a morphogen produced by the cells of that tissue.

For purposes of the present invention, the above-described morphogens effective in alleviating ischemic-reperfusion injury (or the agents that stimulate them, referred to herein collectively as "therapeutic agent") are administered prior to or during the restoration of oxygen (e.g., restoration of blood flow, reperfusion.) Where treatment is to follow an existing injury, the therapeutic agent preferably is administered as an intravenous infusion provided acutely after the hypoxic or ischemic condition occurs. For example, the therapeutic agent can be administered by intravenous infusion immediately after a cerebral infarction, a myocardial infarction, asphyxia, or a cardiopulmonary arrest. Where ischemia or hypoxia is deliberately induced as part of, for example, a surgical procedure where circulation to an organ or organ system is deliberately and/or transiently interrupted, e.g., in carotid enterectomy, coronary artery bypass, grafting, organ transplanting, fibrinolytic therapy, etc., the therapeutic agent preferably is provided just prior to, or concomitant with, reduction of oxygen to the tissue. Preferably, the therapeutic agent is administered prophylactically in a surgical setting.

Similarly, where hyperoxia induced-injury already has occurred, the morphogen is administered upon diagnosis. Where hyperoxia may be induced as, for example, during treatment of prematurely newborn babies, or patients suffering from pulmonary diseases such as emphysema, the therapeutic agent preferably is administered prior to administration of oxygen (e.g., prophylactically).

III. EXAMPLES

Example 1
Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) *PNAS* 86:4554–4558 for a description of the cDNA sequence). Similarly, particularly useful mOP-1-specific probe sequences are the BstX1-BglI fragment, a 0.68 Kb sequence that covers approximately two-thirds of the mOP-1 pro region; a StuI—StuI fragment, a 0.2 Kb sequence immediately upstream of the 7-cysteine domain; and the EarI-PstI fragment, an 0.3 Kb fragment containing a portion of the 3'untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al.

((1987) *Anal. Biochem* 162:156–159) and described below. Poly (A)+RNA is prepared by using oligo (dT)-cellulose chromatography (e.g., Type 7, from Pharmacia LKB Biotechnology, Inc.). Poly (A)+ RNA (generally 15 pg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5× SSPE, and 0.1% SDS. Following hybridization, the non-specific counts are washed off the filters in 0.1× SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 752,764, and in Ozkaynak, et al., (1991) *Biochem. Biophys. Res. Commn.* 179:116–123, and Ozkaynak, et al. (1992) (JBC, in press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. OP-1 RNA also was identified in salivary glands, specifically rat parotid glands, using this probing methodology. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2
Active Morphogens in Body Fluids

OP-1 expression has been identified in saliva (specifically, the rat parotid gland, see Example 1), human blood serum, and various milk forms, including mammary gland extract, colostrum, and 57-day bovine milk. Moreover, and as described in U.S. Ser. No. 923,780, the disclosure of which is incorporated herein by reference, the body fluid-extracted protein is morphogenically active. The discovery that the morphogen naturally is present in milk and saliva, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, suggests that the protein may play a significant role in tissue development, including skeletal development, of juveniles.

2.1 Morphogen Detection in Milk

OP-1 was partially purified from rat mammary gland extract and bovine colostrum and 57 day milk by passing these fluids over a series of chromatography columns: (e.g., cation-exchange, affinity and reverse phase). At each step the eluant was collected in fractions and these were tested for the presence of OP-1 by standard immunoblot. Immunoreactive fractions then were combined and purified further. The final, partially purified product then was examined for the presence of OP-1 by Western blot analysis using OP-1-specific antisera, and tested for in vivo and in vitro activity.

OP-1 purified from the different milk sources were characterized by Western blotting using antibodies raised against OP-1 and BMP2. Antibodies were prepared using standard immunology protocols well known in the art, and as described generally in Example 15, below, using full-length E. coli-produced OP-1 and BMP2 as the immunogens. In all cases, the purified OP-1 reacted only with the anti-OP-1 antibody, and not with anti-BMP2 antibody.

The morphogenic activity of OP-1 purified from mammary gland extract was evaluated in vivo essentially following the rat model assay described in U.S. Pat. No. 4,968,590, hereby incorporated by reference. Briefly, a sample was prepared from each OP-1 immunoreactive fraction of the mammary gland extract-derived OP-1 final product by lyophilizing a portion (33%) of the fraction and resuspending the protein in 220 μl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation as described in U.S. Pat. No. 4,968,590. In all cases, the immunoreactive fractions were osteogenically active.

2.2 Morphogen Detection in Serum

Morphogen may be detected in serum using morphogen-specific antibodies. The assay may be performed using any standard immunoassay, such as Western blot (immunoblot) and the like. Preferably, the assay is performed using an affinity column to which the morphogen-specific antibody is bound and through which the sample serum then is poured, to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and the results confirmed by N-terminal sequencing. Preferably, the affinity column is prepared using monoclonal antibodies. Morphogen concentrations in serum or other fluid samples then may be determined using standard protein quantification techniques, including by spectrophotometric absorbance or by quantitation of conjugated antibody.

Presented below is a sample protocol for identifying OP-1 in serum. Following this general methodology other morphogens may be detected in body fluids, including serum. The identification of morphogen in serum further indicates that systemic administration is a suitable means for providing therapeutic concentrations of a morphogen to an individual, and that morphogens likely behave systemically as endocrine-like factors. Finally, using this protocol, fluctuations in endogenous morphogen levels can be detected, and these altered levels may be used as an indicator of tissue dysfunction. Alternatively, fluctuations in morphogen levels may be assessed by monitoring morphogen transcription levels, either by standard northern blot analysis as described in Example 1, or by in situ hybridization, using a labelled probe capable of hybridizing specifically to morphogen "mRNA", and standard RNA hybridization protocols well described in the art and described generally in Example 1.

OP-1 was detected in human serum using the following assay. A monoclonal antibody raised against mammalian, recombinantly produced OP-1 using standard immunology techniques well described in the art and described generally in Example 15, was immobilized by passing the antibody over an aqarose-activated gel (e.g., Affi-Gel™, from Bio-Rad Laboratories, Richmond, Calif., prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP-1 by standard immunoblot using an OP-1 specific antibody as for Example 2.A.

Administered or endogenous morphogen levels may be monitored in the therapies described herein by comparing the quantity of morphogen present in a body fluid sample with a predetermined reference value, for example, to evaluate the efficiency of a therapeutic protocol, and the like. In addition, fluctuations in the level of endogenous morphogen antibodies may be detected by this method, most likely in serum, using an antibody or other binding protein capable of interacting specifically with the endogenous morphogen antibody. Detected fluctuations in the levels of the morphogen or endogenous antibody may be used, for example, as indicators of a change in tissue status. For example, as damaged tissue is regenerated and the tissue or organ's function returns to "normal" and, in the absence of additional tissue damage, lower doses of morphogen may be required, and a higher level of circulating morphogen antibody may be measured.

Example 3
Effect of Morphogen after the Onset of the Ischemic Process

The cardioprotective effect of morphogens following ischemic-reperfusion injury in a mammal can readily be assessed in a rat model. In this example, morphogen (e.g., OP-1) is administered just prior to the onset of the ischemic process in experimentally-induced myocardial infracted rats, essentially following the method of Lefer, et al. (1990) Science 249:61–64 and (1992) J. Mol. Cell. Cardiol. 24: 385–393, the disclosures of which are hereby incorporated by reference. Briefly, loss of myocardial tissue function following ischemia and reperfusion is assayed by measuring loss of myocardial creatine kinease activity (CK) and loss of endothelium-dependent vasorelaxation function (see Example 4, below).

In a first group of ether-anesthetized rats, the left coronary artery was occluded just proximal to the first main branch with a silk ligature to induce a myocardial infarction (MI). The ligature was removed 10 minutes after occlusion to allow for coronary reperfusion. This first group is referred to herein as the "myocardial infarcted" (MI) group. A second group of rats underwent the same procedure except that the coronary artery was not occluded, and thus no myocardial infarction occurred. The second group of rats is referred to herein as the "sham myocardial infarcted group" (SHAM MI).

The first group of rats, the MI group of rats, further was divided into three sup-groups. 2 μg of morphogen (OP-1) were injected intravenously into the first sub-group of MI rats 10 minutes after ligature, immediately before reperfusion; into the second sub-group of MI rats 20 μg of OP-1 were injected intravenously 10 minutes after ligature and immediately before reperfusion; and into the third sub-group of MI rats (control) was injected vehicle only, e.g., 0.9% NaCl, as for the OP-1 treated rats.

Twenty-four hours later, the hearts were removed from all of the rats and the levels of creatine kinase (CK) from the left ventricle (the infarcted region) and from the interventricular septum (the control nonischemic region) were determined by standard means. By comparing the difference in CK activities in both regions, the amount of CK activity lost from the infarcted region was used as an index of cardiac cellular injury to the infarcted region.

As shown in FIG. 1, the data indicate that morphogens (e.g., OP-1) can provide significant cardioprotective effect when provided to ischemic tissue. In the figure, CK loss is graphed as the difference in specific CK activity between the interventricular septum and the left ventricle.

The loss of CK activity by the subgroup of MI rats which received 2 μg of OP-1 just before reperfusion showed some protection as compared with the control MI rats which received injections of vehicle alone, when the levels from both subgroups are measured against, and compared to, the levels obtained for the SHAM MI control. Significant cardioprotection was observed in the subgroup of MI rats which received 20 μg of OP-1 immediately before reperfusion as compared with the control MI rats which received injections of vehicle alone, when the levels from both subgroups are measured against, and compared to, the levels contained within the SHAM MI control.

These data indicate that OP-1 offers significant cardiac protection when administered after ischemia and before reperfusion.

A variation of this example also may be performed providing morphogen to the animal prior to induction of ischemia. The experiments may be performed both in normal and immune-compromised rats to assess the cardioprotective effects of morphogen administered prior to ischemia.

Example 4
Vasodilation of Myocardial Infarcted Cardiac Tissue Treated with Morphogen Certain vasodilators like acetylcholine (ACh) and adenosine diphosphate (ADP, an immune mediator) exert their vasodilation activity only in the presence of intact endothelium, which is stimulated to release a substance termed endothelium-derived relaxing factor (EDRF). If the endothelium is injured so that EDRF is not released, no vasodilation occurs in response to these endothelium-dependent agents. In contrast, several other vasodilators including nitroglycerine (NTG) and nitroprusside, are endothelium-independent dilators, as they dilate blood vessels directly.

The present example demonstrates the ability of OP-1 to prevent the loss of cardioendothelium-dependent relaxation (EDR) activity in the coronary microvasculature following reperfusion of ischemic myocardium, and their ability to reduce myocardial injury 24 hours after morphogen treatment. Briefly, 2 or 24 hours after morphogen treatment ischemia-reperfusion injury is induced in isolated rat hearts, the reperfused hearts are are vasodilated with either ACh or NTG. In the absence of morphogen treatment, injured tissue should inhibit ACh-induced vasodilation, but not NTG-induced vasodilation. Morphogen treatment in expected to enhance ACh-induced vasodilation in the reperfused hearts.

Accordingly, 48 adult male Sprague-Dawley rats (250–330 g) were divided into eight groups of 6 rats each.

Twelve rats were subjected to sham myocardial infarcts (SHAM MI) as described in Example 3. The hearts of the remaining 36 rats were isolated as follows: one set of twelve rats was injected intravenously with OP-1 24 hours prior to isolation of the heart; another set of rats was injected intravenously with 20 μg of OP-1 2 hours prior to isolation of the heart; the final group of rats was injected with vehicle only (e.g., 0.9% NaCl.). The rats then were anesthetized with pentobarbital sodium (35 mg/kg, intraperitonial); their hearts were isolated and perfused by the Langendorff method at a constant flow (15 ml/min) with oxygenated Krebs-Henseleit solution (Aoki et al. (1988) *J. Pharmacol.* 95:35).

Each group of rats then were divided into two subgroups of six rats each. Twenty minutes before reperfusion, coronary vasodilator response was measured by inducing constriction with 0.05 μmol U-44619 (9,11-methanoepoxyprostaglandin $H_2$) followed by a vasodilating agent 3 minutes later: subgroup one 3–15 nmol ACh; subgroup 2–15 nmol NTG and the increase in coronary perfusion pressure (CPP) level measured as an indication of vasodilation. When CPP levels returned to normal, the hearts were subjected to ischemia by reducing coronary infusion to 15% of control flow for 30 minutes, then reestablishing normal flow, i.e., reperfusion, for an additional 20 minutes.

The vasodilator reponse then was remeasured by constriction and administration of vasodilating agent as described above.

Figure 2:
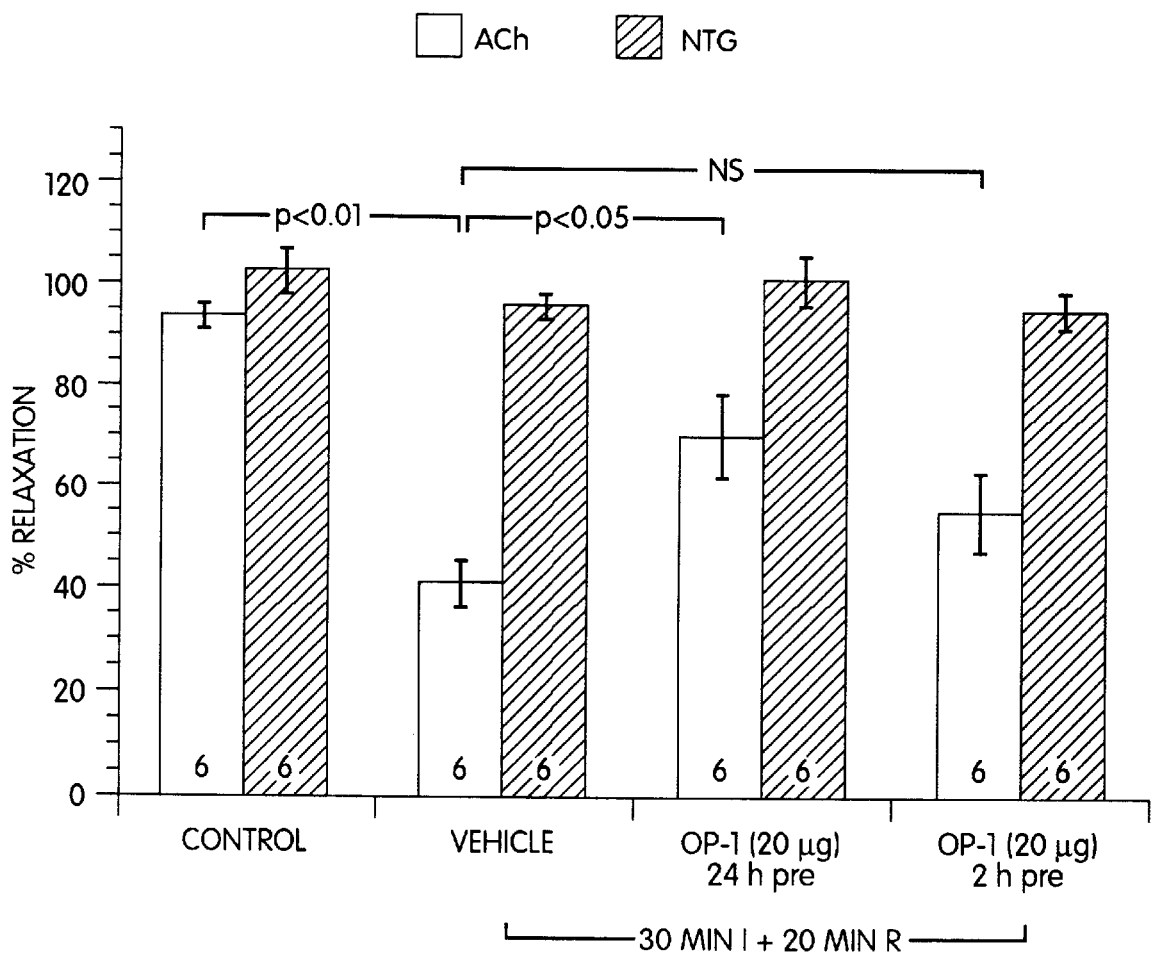
FIG. 2 shows the effects of 20 μg of morphogen (hOP1 given 24 hours prior to isolation of rat heart on endothelial-dependent vasorelaxation to acetycholine following induced ischemia-reperfusion injury.

The results of these experiments are shown in FIG. 2. Before the ischemic event, both Ach and NTG gave normal vasorelaxant results in all events. The hearts which received OP-1 24 hours prior to ischemia showed an approximately 70% response to ACh while the hearts which received OP-1 2 hours prior to ischemia showed a 55% response to ACh. The group which received vehicle alone showed a 40% response to ACh. Finally, the control group which was not subjected to ischemia showed an ACh response of approximately 95%. This shows that endothelium-dependent vasodilators exert a reduced vasodilator response following ischemia and reperfusion in the rat heart. Moreover, OP-1 significantly preserved endothelium-dependent dilation when provided 24 hours prior to induction of myocardial ischemia. No defect in vasodilation occurred in response to the direct vasodilator (NTG); NTG-induced vasodilation activities were 95% of initial in hearts subject to ischemia and 100% of initial nonischemic hearts.

Example 5
Effect of Morphogen on Neutrophil Adherence

The role of neutrophil adherence in endothelium dysfunction and the cardioprotective effects of morphogens in modulating this activity can be assessed using a standard polymorphonuclear neutrophil (PMN) adherence assay such as described in Lefer et al., (1992) *J. Mol. Cell. Cardiol.* 24: 385–393, disclosed hereinabove by reference. Briefly, segments of superior mesenteric artery were isolated from rats which had either been treated with morphogen (OP-1, 20 μg) or 0.9% NaCl, 24 h prior to isolation of the artery. The segments were cleaned, cut into transverse rings of 1–2 mm in length, and these were subsequently cut open and incubated in K-H solution at 37° C., pH 7.4. Neutrophils were prepared and fluorescently labelled using standard procedures (e.g., leukocytes were isolated from rats essentially following the procedure of Pertroft et. al. (1968) *Exp Cell Res* 50: 355–368, washed in phosphate buffered saline (PBS), purified by gradient centrifugation; and labelled by the method of Yuan et. al. (1990) *Microvasc Res* 40: 218–229.

Labelled neutrophils then were added to open ring baths and activated with 100 nM leukotriene $B_4$ ($LTB_4$). Rings were incubated for 20 minutes and the number of neutrophils adhering to the endothelial surface then determined visually by fluorescent microscopy.

Figure 3:
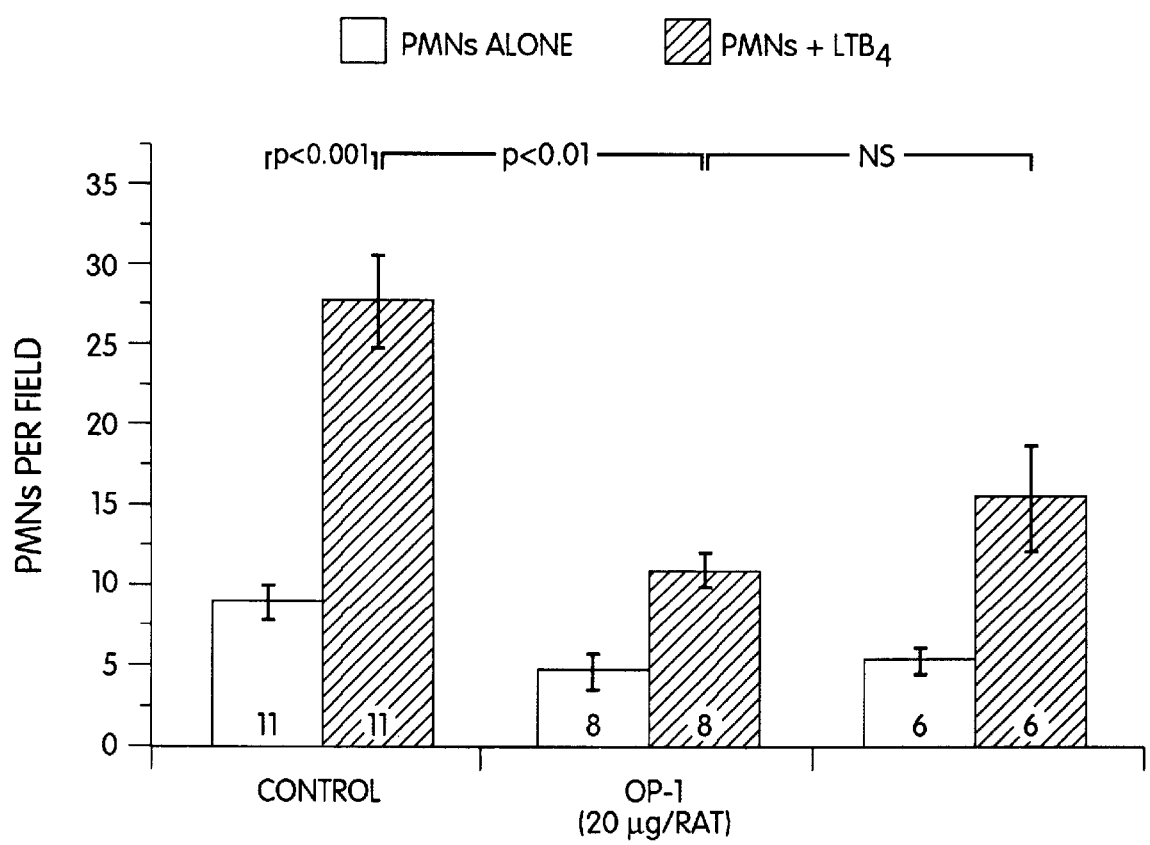
FIG. 3 shows the effect of morphogen (hOP1) on neutrophil adherence to $LTB_4$-stimulated mesenteric artery endothelium in neutrophil-activated rats.

As shown in FIG. 3, unstimulated PMNs (i.e., PMNs alone) added to the baths did not significantly adhere to the vascular endothelium. In rings taken from rats injected with 0.9% NaCl, activation of neutrophils with $LTB_4$ (100 nM) greatly increased the number of PMNs adherent to the endothelium (P<0.001). OP-1 (20 μg administered 24 h prior) significantly inhibited adherence of PMNs activated by $LTB_4$ (P<0.01 from control).

Example 6
In Vivo Models for Ischemic-Reperfusion Protection in Lung, Nerve and Renal Tissue.

Other tissues seriously affected by ischemic-reperfusion injury include neural tissue, renal tissue and lung tissue. The effect of morphogens on alleviating the ischemic-reperfusion injury in these tissues may be assessed using methodologies and models known to those skilled in the art, and disclosed below. Similarly, a methodology also is provided for assessing the tissue-protective effects of a morphogen on damaged lung tissue following hyperoxia injury.

For example, the rabbit embolic stroke model provides a useful method for assessing the effect of morphogens on tissue injury following cerebral ischemia-reperfusion. The protocol disclosed below is essentially that of Phillips et al. (1989) *Annals of Neurology* 25:281–285, the disclosure of which is herein incorporated by reference. Briefly, white New England rabbits (2–3 kg) are anesthesized and placed on a respirator. The intracranial circulation then is selectively catheterized by the Seldinger technique. Baseline cerebral angiography then is performed, employing a digital substration unit. The distal internal carotid artery or its branches then is selectively embolized with 0.035 ml of 18-hour-aged autologous thrombus. Arterial occlusion is documented by repeat angiography immediately after embolization. After a time sufficient to induce cerebral infarcts (15 minutes or 90 minutes), reperfusion is induced by administering a bolus of a reperfusion agent such as the TPA analogue Fb-FB-CF (e.g., 0.8 mg/kg over 2 minutes).

The effect of morphogen on cerebral infarcts can be assessed by administering varying concentrations of morphogens, e.g., OP1, at different times preceding or following embolization and/or reperfusion. The rabbits are sacrificed 3–14 days post embolization and their brains prepared for neuropathological examination by fixing by immersion in 10% neutral buffered formalin for at least 2 weeks. The brains then are sectioned in a coronal plane at 2–3 mm intervals, numbered and submitted for standard histological processing in paraffin, and the degree of neutral tissue necrosis determined visually.

The renal-protective effects of morphogens on renal ischemia-reperfusion injury readily can be assessed using the mouse model disclosed by Oueliette, et al. (1990), *J. Clin. Invest.* 85:766–771, the disclosure of which is hereby incorporated by reference. Briefly, renal ischemia is induced surgically in 35–45 days old out-bred Swiss male mice by performing a standard right nephrectomy, and occluding the artery to the left kidney with a microaneurism clamp for 10–30 minutes. Morphogen then may be provided parentally at various times prior to or following, occlusion and/or reperfusion. The effects of morphogen then may be assessed by biological and histological evaluation using standard techniuques well known in the art.

The tissue protective effects of morphogen on tissue exposed to lethally high oxygen concentrations may be assessed by the following procedure. Adult rats (275–300 gms) first are provided with morphogen (e.g., hOP1) or vehicle only, and then are exposed to 96–98% oxygen essentially as described by Rinaldo et al (1983) *Am. Rev. Respir. Dis.* 130:1065, to induce hyperoxia. Animals are housed in plastic cages (38 cm×48 xm×21 cm). A cage containing 4–5 animals is placed in a 75 liter water-sealed plexiglass chamber. An atmosphere of 96–98% oxygen then is maintained by delivery of $O_2$ gas (liquid $O_2$). Gas flow through the chamber is adjusted to maintain at least 10 air changes/hr., temperature at 22±1° C., minimal levels of condensation within the cage, and carbon dioxide concentration of <0.5% as measured with a mass spetrophotometric medical as analyzer.

At the end of 72 hours all survivors are observed at room air for 1.5 hours and at longer time periods to assess degree of respiratory distress and cyanosis induced by the initial insult and subsequent immune insult and subsequent immune cell-mediated damage. The number of survivors at the end of the challenge is recorded and the treated groups compared with the untreated control group by chi-square test of proportions. Several of the surviving animals for each group are randomly chosen for histological processing of lung tissue.

Lung tissue for histological processing is fixed by infusion of 10% buffered formalin through a tracheal cannula at a constant pressure of 20 cm $H_2O$. After fixation for 24–48 hours, sections from each lobe are cut and subsequently stained with hematoxylin and eosin. Coded slides then are examined, preferably in a double-blind fashion for evidence of pathological changes such as edema, interstitial cellularity, and inflammatory response.

Example 7
Morphogen Inhibition of Cellular and Humoral Inflammatory Response

Figure 4B:
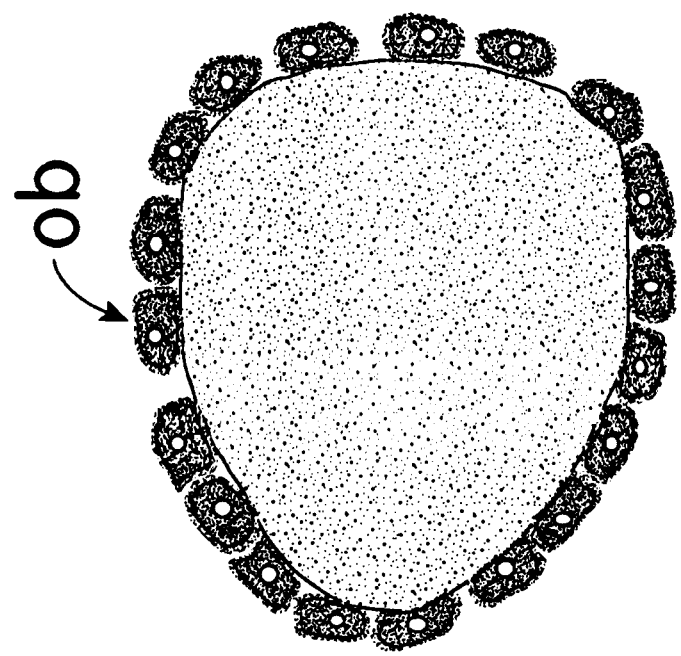
FIGS. 4 (A and B) are schematic representations of morphogen inhibition of early mononuclear phagocytic multinuclearization in vivo.
Figure 4A:
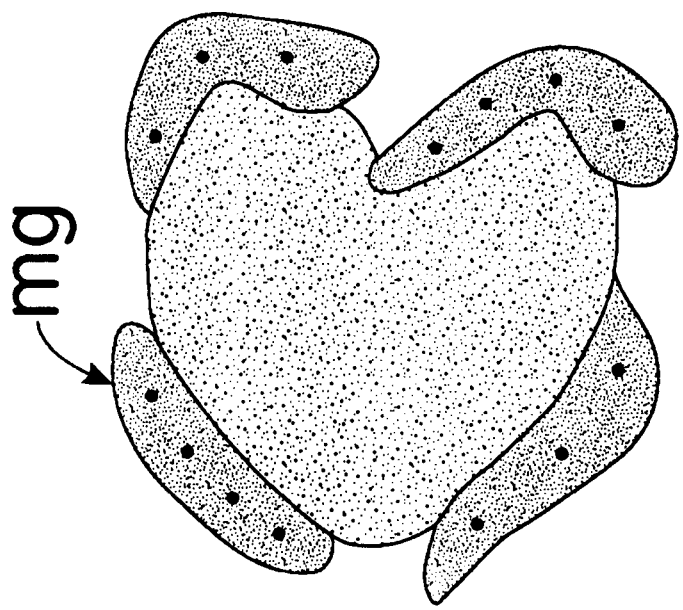

Morphogens described herein inhibit multinucleation of mononuclear phagocytic cells under conditions where these cells normally would be activated, e.g., in response to a tissue injury or the presence of a foreign substance. For example, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. FIG. 4 illustrates this effect of morphogens, in a schematic representation of histology results of a titanium oxide substrate implanted subcutaneously. In the figure, "mg" means mononuclear giant cells and "ob" means osteoblasts. The substrate represented in FIG. 4B was implanted together with morphogen (OP-1) and newly formed osteoblasts are evident surrounding the substrate. By contrast, the substrate represented in FIG. 4A was implanted without morphogen and extensive multinucleated giant cell formation is evident surrounding the substrate. Accordingly, the morphogens' effect in inhibiting excessive bone mass loss in a mammal also may include inhibiting activation of these cells.

In addition, the morphogens described herein also suppress antibody production stimulated in response to a foreign antigen in a mammal. Specifically, when bovine bone collagen matrix alone was implanted in a bony site in a rat, a standard antibody response to the collag,n is stimulated in the rat as determined by standard anti-bovine collagen ELISA experiments performed on blood samples taken at four week intervals following implantation (e.g., between 12 and 20 weeks.) Serum anti-collagen antibody titers, measured by ELISA essentially following the procedure described by Nagler-Anderson et al, (1986) *PNAS* 83:7443–7446, the disclosure of which is incorporated herein by reference, increased consistently throughout the experiment. However, when the matrix was implanted together with a morphogen (e.g., OP-1, dispersed in the matrix and adsorbed thereto, essentially as described in U.S. Pat. No. 4,968,590) anti-bovine collagen antibody production was suppressed significantly. This ability of morphogen to suppress the humoral response is further evidence of morphogen utility in alleviating tissue damage associated with autoimmune diseases, including autoantibody diseases, such as rheumatoid arthritis.

Example 8
Morphogen protection of Gastrointestinal Tract Mucosa from Ulceration and Inflammation Oral mucositis is a gastrointestinal tract inflammatory disease which involves ulcerations of the mouth mucosa as a consequence of, e.g., radiation therapy or chemotherapy. While not typically a chronic disease, the tissue destructive effects of oral mucositis mirror those of chronic inflammatory diseases such as IBD. The example below demonstrates morphogen efficacy in protecting the oral mucosa from oral mucositis in a hamster model, including both inhibiting inflammatory ulceration and enhancing regeneration of ulcerated tissue, retails of the protocol can be found in Sonis, et al., (1990) *Oral Surg. Oral Med. Oral Pathol* 69: 437–443, the disclosure of which is incorporated herein by reference. Based on these data, the morphogens described herein should be efficacious in treating chronic inflammatory diseases including IBD, arthritis, psoriasis and psoriatic arthritis, multiple sclerosis, and the like.

Golden syrian hamsters (6–8 wks old, Charles River Laboratories, Wilmington, Mass.) were divided into 3 test groups: Group 1, a placebo (e.g., saline) control, and a morphogen low dose group (100 ng) and a morphogen high dose group (1 μg), Groups 2 and 3, respectively. Morphogen dosages were provided in 30% ethanol. Each group contained 12 animals.

Beginning on day 0 and continuing through day 5, Groups 2 and 3 received twice daily morphogen applications. On day 3, all groups began the mucositis-induction procedure. 5-fluorouracil (60 mg/kg) was injected intraperitoneally on days 3 and 5. On day 7, the right buccal pouch mucosa was superficially irritated with a calibrated 18 gauge needle. In untreated animals, severe ulcerative mucositis was induced in at least 80% of the animals by day 10.

For each administration of the vehicle control (placebo) or morphogen, administration was performed by first gently drying the cheek pouch mucosa, then providing an even application over the mucosal surface of the vehicle or morphogen material. A hydroxypropylcellulose-based coating was used to maintain contact of the morphogen with the mucosa. This coating provided at least 4 hours of contact time.

On day 12, two animals in each group were sacrificed for histological studies. The right buccal pouch mucosa and underlying connective tissue were dissected and fixed in 10% formalin using standard dissection and histology procedures. The specimens were mounted in paraffin and prepared for histologic examination. Sections then were stained with hematoxylin and eosin and were examined blindly by three oral pathologists with expertise in hamster histology and scored blind against a standard mucositis panel. The extent of atrophy, cellular infiltration, connective tissue breakdown, degree of ulceration and epithelialization were assessed.

The mean mucositis score for each group was determined daily for each experimental group for a period of 21 days by photography and visual examination of the right buccal cheek pouch. Differences between groups were determined using a standard 't' test, e.g., the Students' 't' test. In addition, data was evaluated between groups by comparing the numbers of animals with severe mucositis using Chi Square statistical analysis. The significance of differences in mean daily weights also was determined.

Figure 5:
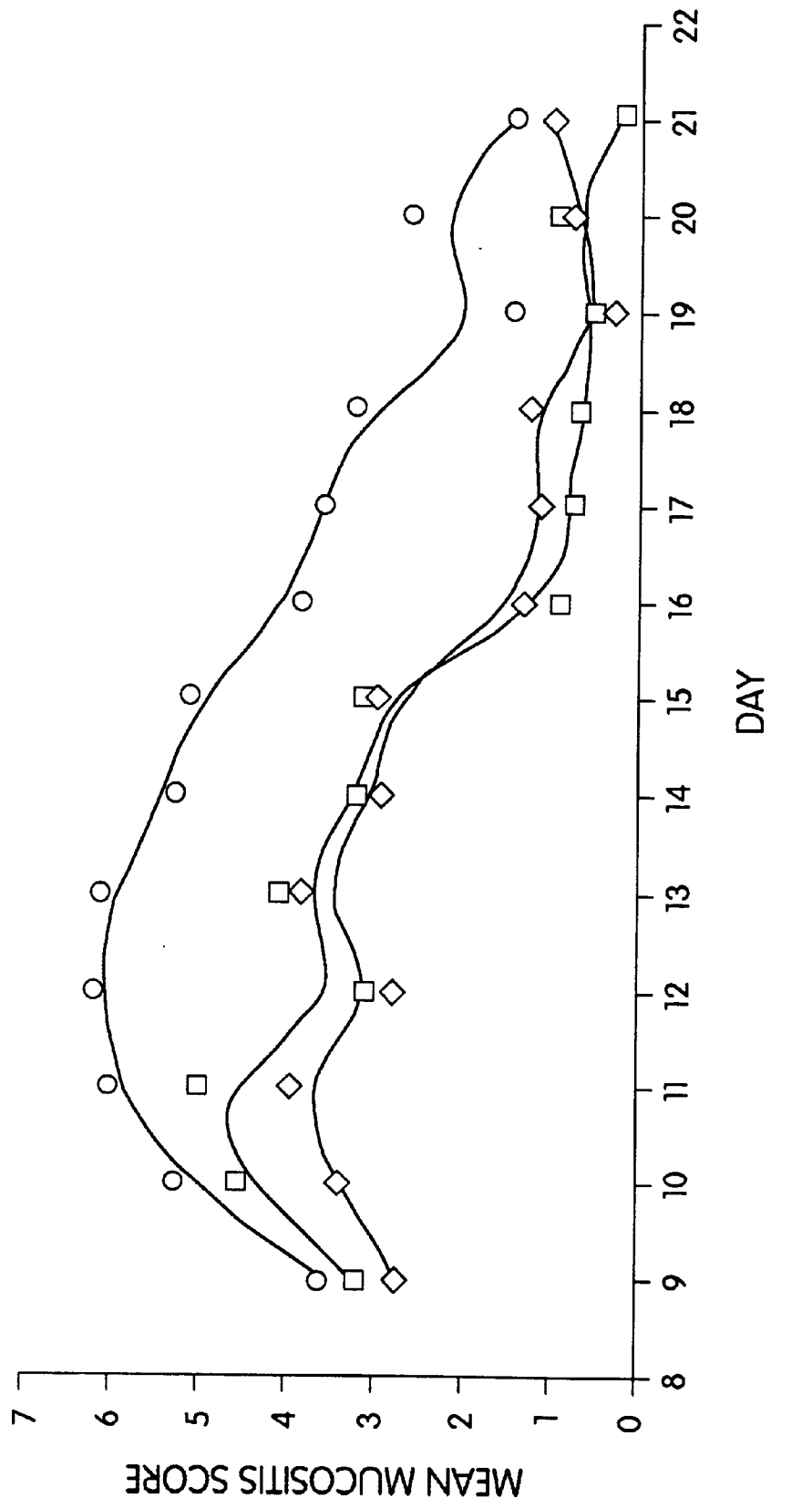
FIG. 5 graphs the effect of a morphogen (e.g., OP-1) and a placebo control on mucositic lesion formation.
Figure 6A:
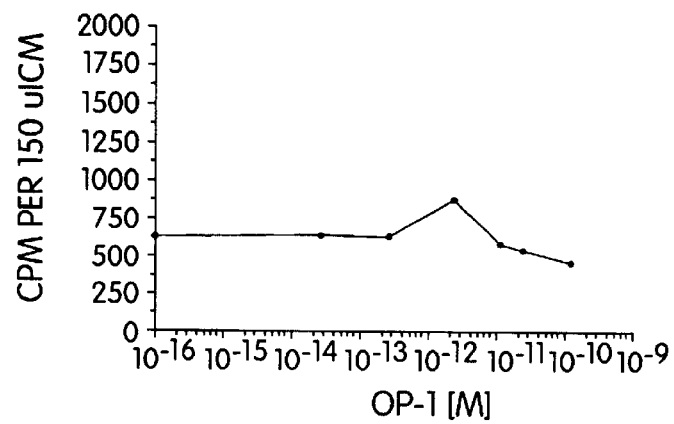
FIGS. 6 (A–D) graphs the effects of a morphogen (eg., OP-1, FIGS. 6A and 6C) and TGF-P (FIGS. 6B and 6D) on collagen (6A and 6B) and hyaluronic acid (6C and 6D) production in primary fibroblast cultures.
Figure 6B:
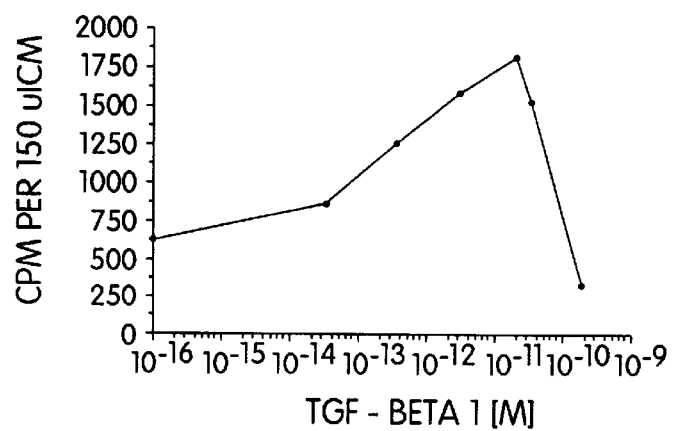
Figure 6C:
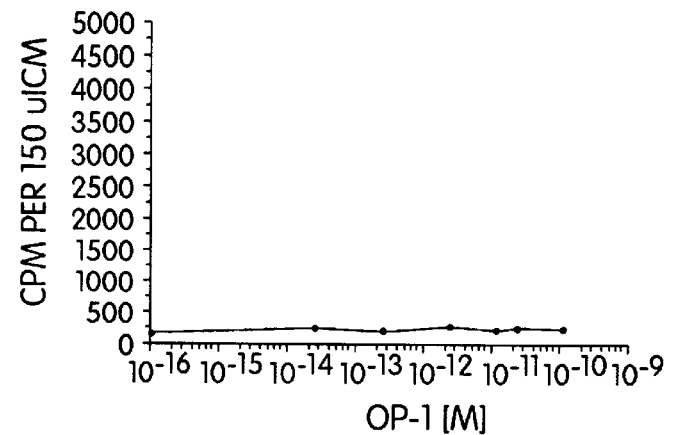
Figure 6D:
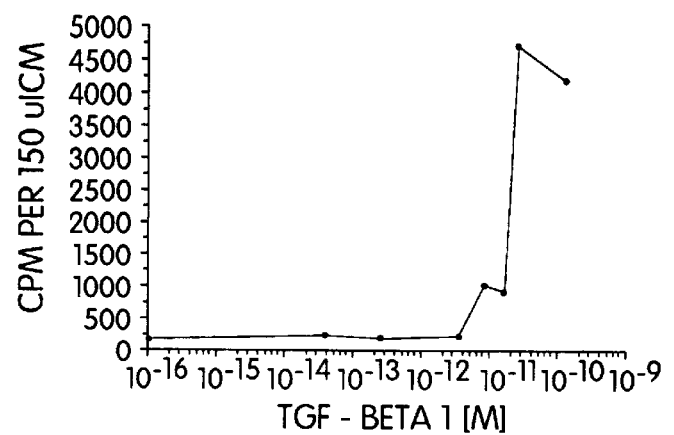

The experimental results are presented in FIG. 5, which graphs the effect of morphogen (high dose, squares; low dose, diamonds) and placebo (circles) on mean mucositis scores. Both low and high morphogen doses inhibit lesion formation significantly in a dose-dependent manner. In addition, histology results consistently showed significantly reduced amounts of tissue atrophy, cellular debris, and immune effector cells, including macrophages and activated neutrophils, in the morphogen-treated animals, as compared with the untreated, control animals.

Example 9
Morphogen Effect on Fibrogenesis and Scar Tissue Formation

The morphogens described herein induce tissue morphogenesis of damaged or lost tissue. The ability of these proteins to regenerate new tissue enhances the anti-inflammatory effect of these proteins. Provided below are a series of in vitro experiments demonstrating the ability of morphogens to induce migration and accumulation of mesenchymal cells. In addition, the experiments demonstrate that morphogens, unlike TGF-β, do not stimulate fibrogenesis or scar tissue formation. Specifically, morphogens do not stimulate production of collagen, hyaluronic acid (HA) or metalloproteinases in primary fibroblasts, all of which are required for fibrogenesis or scar tissue formation. By contrast, TGF-β, a known inducer of fibrosis, but not of tissue morphogenesis, does stimulate production of these fibrosis markers.

Chemotaxis and migration of mesenchymal progenitor cells were measured in modified Boyden chambers essentially as described by Fava, R. A. et al (1991) *J. Exp. Med.* 173: 1121–1132, the disclosure of which is incorporated herein by reference, using polycarbonate filters of 2, 3 and 8 micron ports to measure migration of progenitor neutrophils, monocytes and fibroblasts. Chemotaxis was measured over a range of morphogen concentrations, e.g., $10^{-1}$ M to $10^{-12}$ M OP-1. For progenitor neutrophils and monocytes, $10^{-18}$–$10^{-17}$ M OP-1 consistently induced maximal migration, and $10^{-14}$ to $10^{-13}$ M OP-1 maximally induced migration of progenitor fibroblasts. In all cases the chemotactic activity could be inhibited with anti-OP-1 antibody. Similar migration activities also were measured and observed with TGF-β.

The effect of morphogen on fibrogenesis was determined by evaluating fibroblast production of hyaluronic acid (HA), collagen, collagenese and tissue inhibitor of metalloproteinases (TIMP).

Human fibroblasts were established from explants of infant foreskins and maintained in monolayer culture using standard culturing procedures. (See, for example, (1976) *J. Exp. Med.* 144: 1188–1203.) Briefly, fibroblasts were grown in maintenance medium consisting of Eagle's MEM, supplemented with nonessential amino acids, ascorbic acid (50 $\mu$g/ml), NaHCO$_3$ and HEPES buffers (pH 7.2), penicillin (100 U/ml), streptomycin (100 $\mu$g/ml), amphotericin B (1 $\mu$g/ml) and 9% heat inactivated FCS. Fibroblasts used as target cells to measure chemotaxis were maintained in 150 mm diameter glass petri dishes. Fibroblasts used in assays to measure synthesis of collagen, hyaluronic acid, collagenase and tissue inhibitors of metalloproteinases (TIMP) were grown in 100 mm diameter plastic tissue culture petri dishes.

The effects of morphogen on fibroblast production of hyaluronic acid, collagens, collagenase and TIMP were determined by standard assays (See, for example, Postteth-waite et dl. (.1989) *J. Clin. Invest.* 83: 629–636, Postteth-waithe (1988) *J./ Cell Biol.* 106: 311–318 and Clark et al (1985) *Arch. Bio-chem Biophys.* 241: 36–44, the disclosures of which are incorporated by reference.) For these assays, fibroblasts were transferred to 24-well tissue culture plates at a density of $8 \times 10^4$ cells per well. Fibroblasts were grown confluency in maintenance medium containing 9% FCS for 72 h and then grown in serum-free maintenance medium for 24 h. Medium was then removed from each well and various concentrations of OP-1 (recombinantly produced mature or soluble form) or TGF-β-1 (R&D Systems, Minneapolis) in 50 $\mu$l PBS were added to triplicate wells containing the confluent fibroblast monolayers. For experiments that measured production of collagenase and TIMP, maintenance medium (450 $\mu$l) containing 5% FCS was added to each well, and culture supernatants were harvested from each well 48 h later and stored at $-70°$ C. until assayed. For experiments that assessed HA production, maintenance medium (450 $\mu$l) containing 2.5% FCS was added to each well, and cultures grown for 48 h. For experiments that measured fibroblast production of collagens, serum-free maintenance medium (450 $\mu$l) without non-essential amino acids was added to each well and cultures grown for 72 h. Fibroblast production of HA was measured by labeling newly synthesized glycosaminoglycans (GAG) with [$^3$H]-acetate the last 24 h of culture and quantitating released radioactivity after incubation with hyaluronidase from *Streptomyces hyalurolyticus* (ICN Biochemicals, Cleveland, Ohio) which specifically degrades hyaluronic acid. Production of total collagen by fibroblasts was measured using a collagenase-sensitive protein assay that reflects [$^3$H]-proline incorporation the last 24 h of culture into newly synthesized collagens. Collagenase and TIMP protein levels in fibroblast cultures supernatants was measured by specific ELISAs.

As shown in FIG. 6, OP1 does not stimulate significant collagen or HA production, as compared with TGF-β. In the figure, panel A shows OP-1 efect on collagen production, panel B shows TGF-β effect on collagen production, and panels C and D show OP-1 (panel C) and TGF-β (panel D) effect on HA production. The morphogen results were the same whether the soluble or mature form of OP1 was used. By contrast, the latent form of TGF-β (e.g., pro domain-associated form of TGF-β) was not active.

Example 10
Morphogen Inhibition of Epithelial Cell Proliferation

This example demonstrates the ability of morphogens to inhibit epithelial cell proliferation in vitro, as determined by $^3$H-thymidine uptake using culture cells from a mink lung epithelial cell line (ATCC No. CCL 64), and standard mammalian cell culturing procedures. Briefly, cells were grown to confluency in Eagle's minimum essential medium (EMEM) supplemented with 10% fetal bovine serum (FBS), 200 units/ml penicillin, and 200 $\mu$g/ml streptomycin, and used to seed a 48-well cell culture plate at a cell density of 200,000 cells per well. When this culture became confluent, the media was replaced with 0.5 ml of EMEM containing 1% FBS and penicillin/streptomycin and the culture incubated for 24 hours at 37 C. Morphogen test samples in EMEM containing 5% FBS then were added to the wells, and the cells incubated for another 18 hours. After incubation, 1.0 µCi of $^3$H-thymidine in 10 µl was added to each well, and the cells incubated for four hours at 37 C. The media then was removed and the cells washed once with ice-cold phosphate-buffer saline and DNA precipitated by adding 0.5 ml of 10% TCA to each well and incubating at room temperature of 15 minutes. The cells then were washed three times with ice-cold distilled water, lysed with 0.5 ml 0.4 M NaOH, and the lysate from each well then transferred to a scintillation vial and the radioactivity recorded using a scintillation counter (Smith-Kline Beckman).

The results are presented in Table III, below. The antiproliferative effect of the various morphogens tested was expressed as the counts of 3H-thymidine (×1000) integrated into DNA, and were compared with untreated cells (negative control) and TGF-β (1 ng), a local-acting factor also known to inhibit epithelial cell proliferation. COP-5 and COP-7 are biosynthetic constructs that previously have been shown to have osteogenic activity, capable of inducing the complete cascade resulting in endochondral bone formation in a standard rat bone assay (see U.S. Pat. No. 5,011,691.) The morphogens significantly inhibit epithelial cell proliferation. Similar experiments, performed with the morphogens COP-16, bOP (bone-purified osteogenic protein, a dimeric protein comprising CBMP2 and OP-1), and recombinant OP-1, also inhibit cell proliferation. bOP and COP-16 also induce endochondral bone formation (see U.S. Pat. Nos. 4,968,590 and 5,011,691.)

TABLE III

|  | Thymidine uptake (×1000) |
| --- | --- |
| control | 50.048, 53.692 |
| COP-7-1 (10 ng) | 11.874 |
| COP-7-2 (3 ng) | 11.136 |
| COP-5-1 (66 ng) | 16.094 |
| COP-5-2 (164 ng) | 14.43 |
| TGF-β (1 ng) | 1.86, 1.478 |

Example 11
Morphogen Treatment of a Systemic Inflammatory Disease

The following example provides a rat adjuvant-induced arthritis model for demonstrating morphogen efficacy in treating arthritis and other systemic inflammatory diseases. Rat adjuvant-induced arthritis induces a systemic inflammatory disease with bone and cartilage changes similar to those observed in rhematoid arthritis, but in an accelerated time span (see, for example, Pearson (1964) *Arth. Rheum.* 7:80). A detailed description of the protocol is provided in Walz, et al., (1971) *J. Pharmac. Exp. Ther.* 178: 223–231, the disclosure of which is incorporated herein by reference.

Briefly, Sprague-Dawley female rats (e.g., Charles River Laboratories, Wilmington, Mass.) are randomized into 3 groups: control; morphogen, low dose (e.g., 1–10 µg/kg weight per day) and morphogen, high dose (e.g., 10–20 µg/kg weight per day), referred to as Groups 1, 2, and 3, respectively.

Adjuvant arthritis is induced in all three groups by injection of 0.05 ml of a suspension of 1.5% dead Mycobacterium butyricum in mineral oil into the subplantar surface of the right hand paw. On Day 18 after adjavant injection, the limb volumes of both hind limbs are determined. In the absence of morphogen treatment, a systemic arthritic condition is induced in the rats by this time, as determined by rats with significant swelling of the uninjected hind limbs (<2.3 ml, volume measured by mercury displacement). Subsequent determinations of paw edema and x-ray scores are made on the uninjected hind limb. Rats in Group 2 and 3 also are dosed orally daily, beginning on Day 1, with morphogen. Limb volumes are recorded on Days 29 and 50 after adjuvant injection and edema determined by volume difference compared to Day 18. The uninjected hind limb on each rat was x-rayed on Day 50 and the joint damage assayed on an arbitrary scale of 1 to 10 (1=no damage, 10=maximum damage). Data on differences between control and treated groups (Day 29 edema, Day 50 edema and Day 50 x-ray scores) are analyzed by using a standard "t-test". Morphogen-treated rats show consistently reduced joint damage (e.g., decreased in edema and in x-ray scores) as compared with untreated control rats.

As another, alternative example, Groups 2 and 3 are dosed daily with morphogen beginning on Day 18 and continuing through Day 50 to demonstrate the efficacy of morphogens in arthritic animals.

Example 12
Morphogen Inhibition of Localized Edema

The following example demonstrates morphogen efficacy in inhibiting a localized inflammatory response in a standard rat edema model. Experimental rats (e.g., Long-Evans from Charles River Laboratories, Wilmington, Mass.) are divided into three groups: Group 1, a negative control, which receives vehicle alone; Group 2, a positive control, to which is administered a well-known characterized anti-inflammatory agent (e.g., indomethacin), and Group 3, to which morphogen is provided.

Groups 2 and 3 may be further subdivided to test low, medium and high doses (e.g., Group 2: 1.0 mg/kg, 3.0 mg/kg and 9.0 mg/kg indomethacin; Group 3: 0.1–5 µg; 5–20 µg, and 20–50 µg of morphogen). Sixty minutes after indomethacin or morphogen is provided to the rats of Group 2 or 3 (e.g., as by injection into the tail vein, or by oral gavage) inflammation is induced in all rats by a sub-plantar injection of a 1% carrageenin solution (50 µl) into the right hind paw. Three hours after carrageenin administration paw thickness is measured as an indication of edema (e.g., swelling) and induced inflammatory response to the injected carrageenin solution.

Significant swelling is evident in untreated rats by three hours after carrageenin injection. Inflammation also is measured by histology by standard means, following euthanasia e.g.: the right hind paw from each animal is removed at the ankle joint and weighed and foot pad tissue is fixed in 10% neutral buffered formalin, and slides prepared for visual examination by staining the prepared tissue with hematoxylin and eosin.

The morphogen-treated rats show substantially reduced edema induction following carrageenin injection as compared with the untreated rats.

Example 13
Morphogen Treatment of Allergic Encephalomyelitis

The following example demonstrates morphogen efficacy in treating experimental allergic encephalomyelitis (EAE) in a rat. EAE is a well-characterized animal model for multiple sclerosis, an autoimmune disease. A detailed description of the protocol is disclosed in Kuruvilla, et al., (1991) *PNAS* 88:2918–2921, the disclosure of which is incorporated herein by reference.

Briefly, EAE is induced in rats (e.g., Long-Evans, Charles River Laboratories, Wilmington, Mass.) by injection of a CNS tissue (e.g., spinal cord) homogenate in complete Freund's adjuvant (CFA) on days −44, −30 and 0 (last day of immunization), by subcutaneous injection to three sites on the animal's back. Morphogen is administered daily by interperitoneal injection beginning on day −31. Preferably, a series of morphogen dose ranges is evaluated (e.g., low, medium and high) as for Example 12, above.) Control rats receive morphogen vehicle only (e.g. 0.9% NaCl or buffered saline). Rats are examined daily for signs of disease and graded on an increasing severity scale of 0–4.

In the absence of morphogen treatment, significant neurological dysfunction (e.g., hind and fore limb weakness, progressing to total hind limb paralysis) is evident by day +7 to +10. Hematology, serum chemistry profiles and histology are performed to evaluate the degree of tissue necropsy using standard procedures. Morphogen treatment significantly inhibits the neurological dysfunction normally evident in an EAE animal. In addition, the histopathological markers typically associated with EAE are absent in the morphogen-treated animals.

Example 14
Morphogen Treatment of Collagen-Induced Arthritis

The following example demonstrates the efficacy of morphogens in inhibiting the inflammatory response in a collagen-induced arthritis (CIA) in a rat. CIA is a well-characterized animal model for rheumatoid arthritis, an autoimmune disease. The protocol disclosed is essentially that disclosed in Kuruvilla et al., (1991) PNAS 88:2918–2921, incorporated by reference hereinabove. Briefly, CIA is induced in experimental rats (e.g., Long-Evans, Charles River Laboratories, Wilmington), by multiple intradermal injection of bovine Type II collagen (e.g., 100 μg) in CFA (0.2 ml) on Day 1. Animals are divided into two groups: Group 1, control animals, which receive vehicle alone, and Group 2: morphogen-treated animals, which, preferably, are subdivided into low, medium and high dose ranges, as described for Example 13, above. Morphogen is administered daily (e.g., by tail vein injection) beginning at different times following collagen injection, e.g., beginning on day 7, 14, 28, 35 and 42. Animals are evaluated visually and paw thickness and body weight is monitored throughout the experiment. Animals are sacrificed on day 60 and the proximal and distal limb joints, and ear, tail and spinal cord prepared for histological evaluation as described for Examples 12 and 13, above. In a variation of the experiment, morphogen may be administered for prescribed periods, e.g., five day periods, beginning at different times following collagen injection (e.g., on days 0–4, 7–11, 14–18, 28–32.)

In the absence of morphogen treatment, an arthritic condition typically is induced by 30 days post collagen injection. In morphogen-treated animals, CIA is suppressed and the histopathological changes typically evidenced in control CIA-induced animals are absent: e.g., accumulations of activated mononuclear inflammatory cells and fibrous connective tissue. In addition, consistent with the results in Example 7, above, serum anti-collagen antibody titers are suppressed significantly in the morphogen-treated animals.

Example 15
Screening Assay for Candidate Compounds which Alter Endogenous Morphogen Levels Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A more detailed description also may be found in U.S. Ser. No. 752,861, incorporated hereinabove by reference.

15.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladders brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for OP-1 production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo OP-1 synthesis, some cultures are labeled according to conventional procedures with an $^{35}$S-methionine/$^{35}$S-cysteine mixture for 6–24 hours and then evaluated to OP-1 synthesis by conventional immunoprecipitation methods.

15.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 μg/100 μl of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 μl aliquot of an appropriate dilution of each of the test samples of cell culture supernatant is added to each well in triplicate and incubated at 37° C. for 30 min. After incubation, 100 μl biotinylated rabbit anti-OP-i serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3 M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 μg/500 μl E. coli produced OP-1 monomer (amino acids 328–431 in SEQ ID NO:5) in 0.1% SDS mixed with 500 μl Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 μg of antigen and bled (15 ml per bleed) at days seven and ten after boosting.

Monoclonal antibody specific for a given morphogen may be prepared as follows. A mouse is given two injections of E. coli produced OP-1 monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 (amino acids 307–431 in SEQ ID NO:5) in four intraperitoneal injections at various times over an eight month period. One week prior to fusion, both mice are boosted intraperitoneally with 100 pg of OP-1 (307–431) and 30 μg of the N-terminal peptide ($Ser_{293}$-$Asn_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for treating immune cell mediated inflammatory or fibrogenic response, the method comprising:
   administering a morphogen other than TGF-$\beta_2$ to tissue affected by immune cell mediated inflammatory or fibrogenic response, said morphogen comprising a dimeric protein having an amino acid sequence selected from the group consisting of
   (i) a sequence having at least 70% amino acid sequence homology with the C-terminal seven cysteine skeleton of human OP-1, amino acids 38–139 of Seq. ID No. 5; and
   (ii) Generic Sequence 6, Seq. ID No. 31;
   wherein said morphogen induces endochondral bone formation in an in vivo assay.

2. A method for preventing immune cell mediated inflammatory or fibrogenic response, the method comprising:
   administering a morphogen other than TGF-$\beta_2$ to tissue affected by immune cell mediated inflammatory or fibrogenic response, said morphogen comprising a dimeric protein having an amino acid sequence selected from the group consisting of
   (i) a sequence having at least 70% amino acid sequence homology with the C-terminal seven cysteine skeleton of human OP-1, amino acids 38–139 of Seq. ID No. 5; and
   (ii) Generic Sequence 6, Seq. ID No. 31;
   wherein said morphogen induces endochondral bone formation in an in vivo assay.

3. The method of claim 1 wherein said response is associated with a condition selected from the group consisting of a chronic inflammatory disease, and an autoimmune disease.

4. The method of claim 3 wherein said inflammatory disease is selected from the group consisting of arthritis, psoriasis, multiple sclerosis, amyotrophic lateral sclerosis, dermatitis, and diabetes.

5. The method of claim 4 wherein said arthritis selected from the group consisting of rheumatoid arthritis, degenerative arthritis, and psoriatic arthritis.

6. The method of claim 1 wherein said response is associated with airway inflammation.

7. The method of claim 6 wherein said airway inflammation is associated with a condition selected from the group consisting of chronic bronchitis, emphysema, idiopathic pulmonary fibrosis, and asthma.

8. The method of claim 1 wherein said response is associated with a generalized acute inflammatory response.

9. The method of claim 8 wherein said inflammatory response comprises adult respiratory distress syndrome.

10. A method for reducing tissue damage associated with ischemia-reperfusion injury, the method comprising:
    administering a morphogen other than TGF-$\beta_2$, said morphogen comprising a dimeric protein having an amino acid sequence selected from the group consisting of
    (i) a sequence having greater than 60% amino acid identity with the C-terminal seven cysteine skeleton of human OP-1, amino acids 38–139 of Seq. ID No. 5; and
    (ii) OPX, Seq. ID No. 29;
    wherein said morphogen induces endochondral bone formation in an in vivo assay.

11. A method for reducing tissue damage associated with hyperoxia injury, the method comprising:

administering a morphogen other than TGF-$\beta_2$, said morphogen comprising a dimeric protein having an amino acid sequence selected from the group consisting of
  (i) a sequence having greater than 60% amino acid identity with the C-terminal seven cysteine skeleton of human OP-1, amino acids 38–139 of Seq. ID No. 5; and
  (ii) OPX, Seq. ID No. 29;

wherein said morphogen induces endochondral bone formation in an in vivo assay.

12. The method of claim 10 wherein said ischemia-reperfusion injury is associated with a condition selected from the group consisting of cardiac arrest, pulmonary occlusion, arterial occlusion, coronary occlusion, embolic stroke, and occlusive stroke.

* * * * *